(12) United States Patent
Ishikawa

(10) Patent No.: US 8,044,184 B2
(45) Date of Patent: Oct. 25, 2011

(54) PROBE AND PRIMER FOR TUBERCLE BACILLUS DETECTION, AND METHOD OF DETECTING HUMAN TUBERCLE BACILLUS THEREWITH

(75) Inventor: Tomokazu Ishikawa, Hyogo (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 833 days.

(21) Appl. No.: 11/587,510

(22) PCT Filed: Apr. 22, 2005

(86) PCT No.: PCT/JP2005/007700
§ 371 (c)(1),
(2), (4) Date: Oct. 25, 2006

(87) PCT Pub. No.: WO2005/103249
PCT Pub. Date: Nov. 3, 2005

(65) Prior Publication Data
US 2008/0241826 A1    Oct. 2, 2008

(30) Foreign Application Priority Data
Apr. 26, 2004    (JP) .................................. 2004-129272

(51) Int. Cl.
C07H 21/02    (2006.01)
C07H 21/04    (2006.01)
(52) U.S. Cl. ................... 536/23.1; 536/24.3; 536/24.33; 435/975
(58) Field of Classification Search ........................ None
See application file for complete search history.

(56) References Cited

U.S. PATENT DOCUMENTS

| | | |
|---|---|---|
| 5,210,015 A | 5/1993 | Gelfand et al. |
| 5,348,855 A | 9/1994 | Dattagupta et al. |
| 5,370,998 A | 12/1994 | Crawford et al. |
| 5,409,818 A | 4/1995 | Davey et al. |
| 5,455,166 A | 10/1995 | Walker |
| 5,470,723 A | 11/1995 | Walker et al. |
| 5,474,796 A * | 12/1995 | Brennan ........................ 427/2.13 |
| 5,538,848 A | 7/1996 | Livak et al. |
| 5,554,517 A | 9/1996 | Davey et al. |
| 5,561,044 A | 10/1996 | Walker et al. |
| 5,597,911 A | 1/1997 | Guesdon et al. |
| 5,629,179 A * | 5/1997 | Mierendorf et al. ......... 435/91.2 |
| 5,652,106 A | 7/1997 | Plikaytis et al. |
| 5,723,591 A * | 3/1998 | Livak et al. ................... 536/22.1 |
| 5,731,150 A | 3/1998 | Sandhu et al. |
| 5,736,365 A | 4/1998 | Walker et al. |
| 5,776,693 A | 7/1998 | Guesdon et al. |
| 5,801,155 A | 9/1998 | Kutyavin et al. |
| 5,807,672 A | 9/1998 | Guesdon et al. |
| 5,837,455 A | 11/1998 | Guesdon et al. |
| 5,925,517 A | 7/1999 | Tyagi et al. |
| 6,063,603 A | 5/2000 | Davey et al. |
| 6,294,328 B1 | 9/2001 | Fleischmann et al. |
| 6,492,121 B2 | 12/2002 | Kurane et al. |
| 2001/0053519 A1 * | 12/2001 | Fodor et al. ........................ 435/6 |
| 2003/0219757 A1 | 11/2003 | Dattagupta et al. |
| 2004/0185455 A1 | 9/2004 | Shimada et al. |

FOREIGN PATENT DOCUMENTS

| | | |
|---|---|---|
| CA | 1340807 C | 11/1999 |
| EP | 0070687 A | 7/1982 |
| JP | A-58-40099 | 3/1983 |
| JP | A-60-500717 | 5/1985 |
| JP | A-62-265999 | 11/1987 |
| JP | A-5-507617 | 11/1993 |
| JP | B-7-114718 | 12/1995 |
| JP | B-2650159 | 5/1997 |
| JP | B-2814422 | 8/1998 |
| JP | A-11-514522 | 12/1999 |
| WO | WO8403285 | 8/1984 |
| WO | WO9716564 | 5/1997 |
| WO | WO0029613 | 5/2000 |
| WO | WO03070981 A2 | 8/2003 |

OTHER PUBLICATIONS

Genbank Accession No. X17348 (Mar. 2, 1993).*
Alcantara-Payawal et al. (J Hepatol. Oct. 1997;27(4):620-7).*
Stratagene ("Gene Characterization Kits" 1988).*
Buck et al. (Biotechniques. Sep. 1997;27(3):528-36).*
Supplemental European search report for International Application No. PCT/JP2005/007700 dated Jul. 21, 2008.
Thierry, D. et al., Characterization of a *Mycobacterium tuberculosis* Insertion Sequence, IS6110, and Its Application in Diagnosis, J. Clinical Microbiology, Dec. 1990, p. 2668-2673, American Society for Microbiology, USA.
Eisenach, K. et al., Polymerase Chain reaction Amplification of a Repetitive DNA Sequence Specific for *Mycobacterium tuberculosis*, J. of Infectious Diseases, 1990, p. 977-981, vol. 161, University of Chicago, Chicago, USA.
English Translation of the International Preliminary report on Patentability (Chapter I) for International Application No. PCT/JP2005/007700 dated Nov. 11, 2006, mailed Nov. 23, 2006.
Bessesen et al., Detection of *Listeria monocytogenes* by Using the Polymerase Chain Reaction, Appl. Environ. Microbiol., vol. 56, No. 9, p. 2930-2932 (1990).

(Continued)

*Primary Examiner* — Christopher M. Babic
(74) *Attorney, Agent, or Firm* — Finnegan, Henderson, Farabow, Garrett & Dunner, LLP

(57) ABSTRACT

An object of the present invention is to provide a novel primer and prove for detecting tubercle bacillus capable of avoiding false positive, and an easy-to-use, rapid and high-sensitivity method for detecting human tubercle bacillus (*Mycobacterium tuberculosis*) using the same. The present invention relates to an oligonucleotide comprising a part of or an entire sequence of the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or a part of or an entire sequence of the complementary sequence thereof, wherein the oligonucleotide has a property of hybridizing with the nucleic acid sequence of IS6110 gene in *Mycobacterium tuberculosis*, a primer and a probe containing the oligonucleotide for detecting *Mycobacterium tuberculosis*, and a method for detecting *Mycobacterium tuberculosis* using the primer and the probe.

22 Claims, 7 Drawing Sheets

OTHER PUBLICATIONS

Kolk et al., Detection of *Mycobacterium tuberculosis* in Clinical Samples by Using Polymerase Chain Reaction and a Nonradioactive Detection System, J. Clin. Microbiol, vol. 30, No. 10, p. 2567-2575 (1992).

Oefner et al., High-Performance Liquid Chromatography for Routine Analysis of Hepatitis C Virus cDNA/PCR Products, BioTechniques, vol. 16, No. 5, p. 898-899, 902-908, (1994).

Thierry, et al., IS6110, an IS-like element of *Mycobacterium tuberculosis* complex, Nucleic Acids Research, vol. 18, No. 1, p. 188 (1990).

PAO et al., Detection and Identification of *Mycobacterium tuberculosis* by DNA Amplification, J. clin. Microbiol., vol. 28, No. 9, p. 1877-1880 (1990).

Brisson-Noel et al., Rapid Diagnosis of Tuberculosis by Amplification of Mycobacterial DNA in Clinical Samples, Lancet, vol. 334, p. 1069-1071 (1989).

Hackel et al., Specific Identification of *Mycobacterium leprae* by the polymerase chain reaction, Molecular and cellular Probes, vol. 4, p. 205-210 (1990).

Woods et al., A rapid method for the detection of potentially viable *Mycobacterium leprae* in human biopsies: a novel application of PCR, FEMS Microbiology Letters, vol. 65, p. 305-310 (1989).

Hance et al., Detection and identification of *mycobacteria* by amplification of mycobacterial DNA, Molecular Microbiogy, vol. 3, No. 7, p. I843-849 (1989).

Kulski et al., Use of a Multiplex PCR to Detect and Identify *Mycobacterium avium* and *M. intracellulare* in Blood culture fluids of AIDS Patients, J. Clin. Microbiol, vol. 33, p. 1 668-674 (1995).

Woolford et al., Sequence heterogeneity of an *mpb70* gene analogue in *Mycobacterium kansasii*, FEMS Microbiol Lett., vol. 148, No. 1, p. 43-48 (1997).

Sjobring et al., Polymerase Chain reaction for Detection of *Mycobacterium tuberculosis*, J. Clin. Microbiol., vol. 28, No. 10, p. 2200-2204 (1990).

Hermans et al., Insertion Element IS986 from *Mycobacterium tuberculosis*: a Useful Tool for Diagnosis and Epidemiology of Tuberculosis, J. Clin. Microbiol., vol. 28, p. 2051-2058 (1990).

Lee et al., DNA amplification by the polymerase chain reaction for the rapid diagnosis of tuberculous meningitis. Comparison of protocols involving three mycobacterial DNA Sequences, IS6110, 65 kDa antigen, and MPB64, Neurological Sciences, vol. 123, p. 173-179 (1994).

Jablonski et al., Preparation of oligodeoxynucleotide-alkaline phospatase conjugates and their use as hybridization probes, Nucleic Acids res., vol. 14, p. 6115-6128 (1986).

Kent et al., Public Health Mycobacteriology, A Guide for the Level III Laboratory, U.W. Department of Health and Human Services, Public Health Service, Center for Disease Control, Alanta, USA, p. 31-55 (1985).

Alcantara-Payawal, et al., Direct detection of *Mycobacterium tuberculosis* using polymerase chain rection assay among patients with hepatic granuloma, J. Hepatology, vol. 27, p. 620-627 (1997).

Hellyer, et al., Quantitative Analysis of mRNA as a Marker for Viability of *Mycobacterium tuberculosis*, J. Clin. Microbiology, vol. 37, No. 2, p. 290-295, Year: 1999.

Cleary, et al., Rapid and specific detection of *Mycobacterium tuberculosis* by Using the Smart Cycler Instrument and a Specific Fluorogenic Probe, J. Clin. Microbiol., vol. 41, No. 10, p. 4783-4786 (2003).

Ritis, et al.; Amplification of IS6110 sequence for detection of *Mycobacterium tuberculosis* complex in HIV-negative patients with fever of unknow origin (FUO) and evidence of extrapulmonary disease, j.Internal Medicine, vol. 248, p. 415-424 (2000).

Tzoanopolous et al., the usefulness of PCR amplification of the IS6110 insertion element of *M. tuberculosis* complex comples in ascitic fluid of patients with peritoneal tuberculosis, Eur. J. Internal Medicine, vol. 14, p. 367-371 (2003).

Extended European Search Report issued Oct. 20, 2010 for EP Application No. 10174146.0.

* cited by examiner

[Fig.1]

[Fig.2]
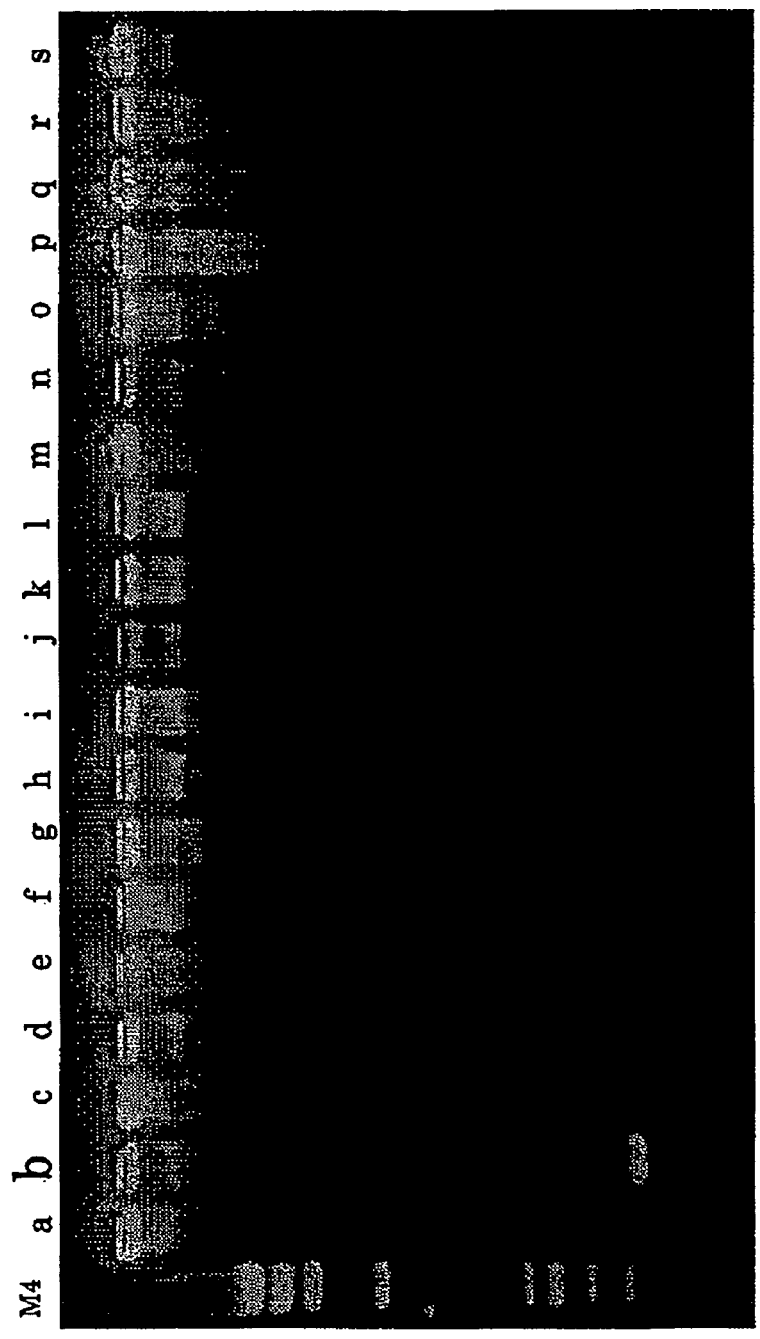

[Fig.3-1]
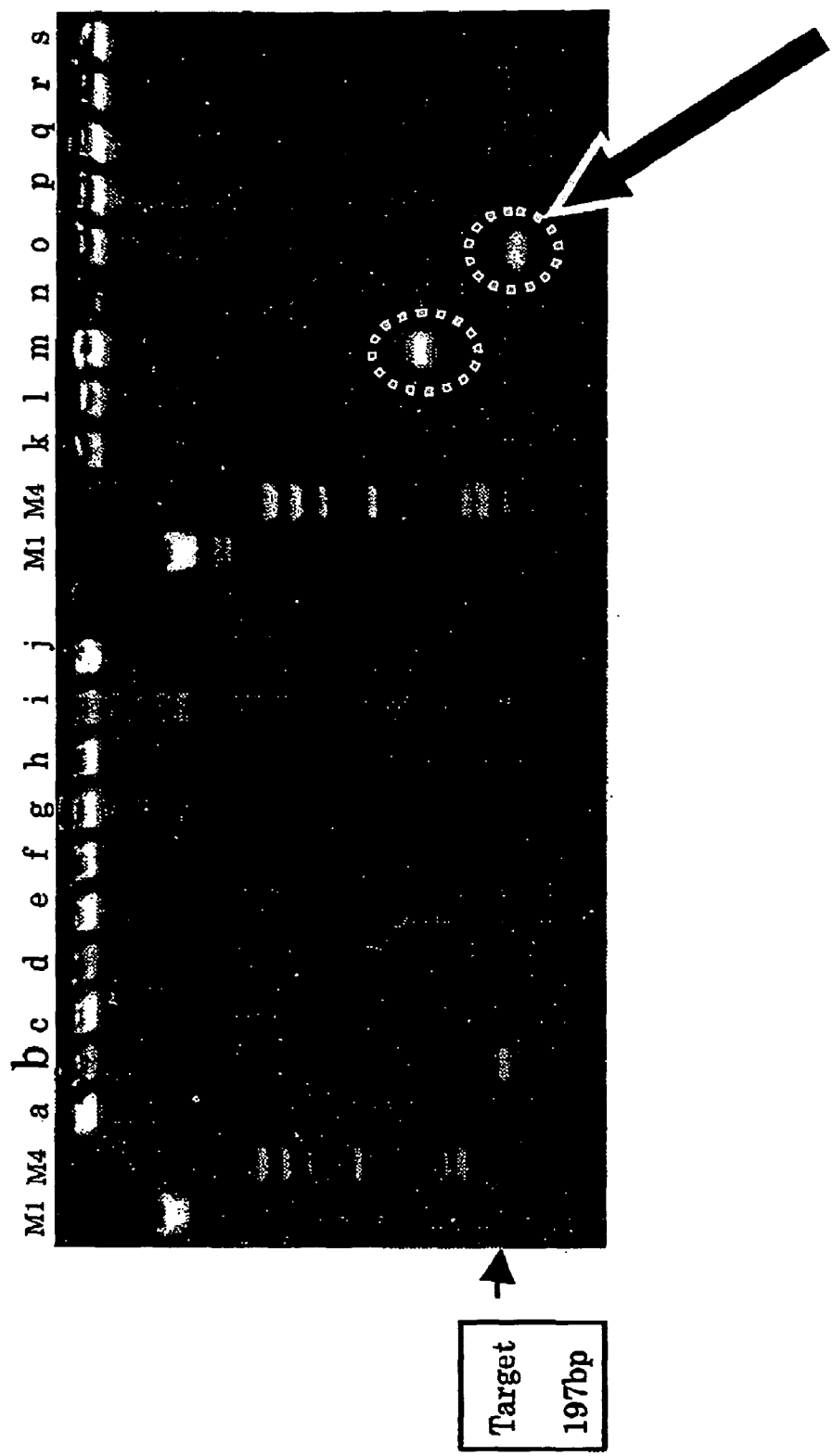

[Fig.3-2]

1st Nucleotide Sequence       (SEQ ID NO:12)
   File Name       : TB_PCRp
   Sequence Size   : 195

2nd Nucleotide Sequence       (SEQ ID NO:13)
   File Name       : triviale_PCRp
   Sequence Size   : 195

[78.462% / 195 bp]    INT/OPT.Score : <    528/    528 >

```
  1' CGGACCACCA GCACCTAACC GGCTGTGGGT AGCAGACCTC ACCTATGTGT CGACCTGGGC
     ********** **********  * *******  ** *** ** ** *******  * ** *** *
  1" CGGACCACCA GCACCTAACC GCTTGTGGGT GGCCGACTTC ACGTATGTGT CCACATGGTC

61' AGGGTTCGCC TACGTGGCCT TTGTCACCGA CGCCTACGCT CGCAGGATCC TGGGCTGGCG
     ** *   * *** ** * * **** *** ********** *** * **** ********
 61" GGGCTGGTGC TACACCGCGT TCGTCATCGA CGCCTACGCC CGCCGCATCC TGGGCTGGTC

121' GGTCGCTTCC ACGATGGCCA CCTCCATGGT CCTCGACGCG ATCGAGCAAG CCATCTGGAC
     *** ** ** ** *** ***  *    **** * *******  **** ** * * ********
121" GGTGGCGACC ACCATGACCA GCCAACTGGT CGTCGACGCC GTCGACCAGG CGATCTGGAC

181' CCGCCAACAA GAAGG (SEQ ID NO:12)
     ********** *****
181" CCGCCAACAA GAAGG (SEQ ID NO:13)
```

[Fig.4]
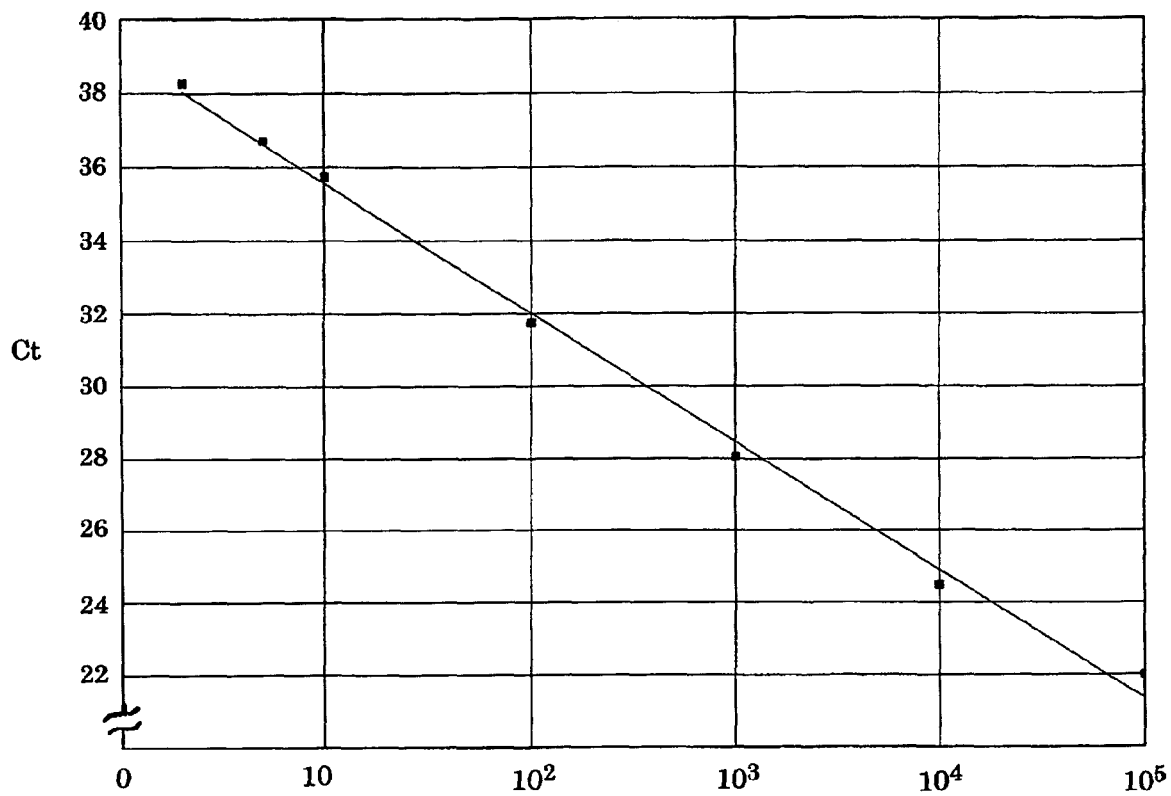

[Fig.5]
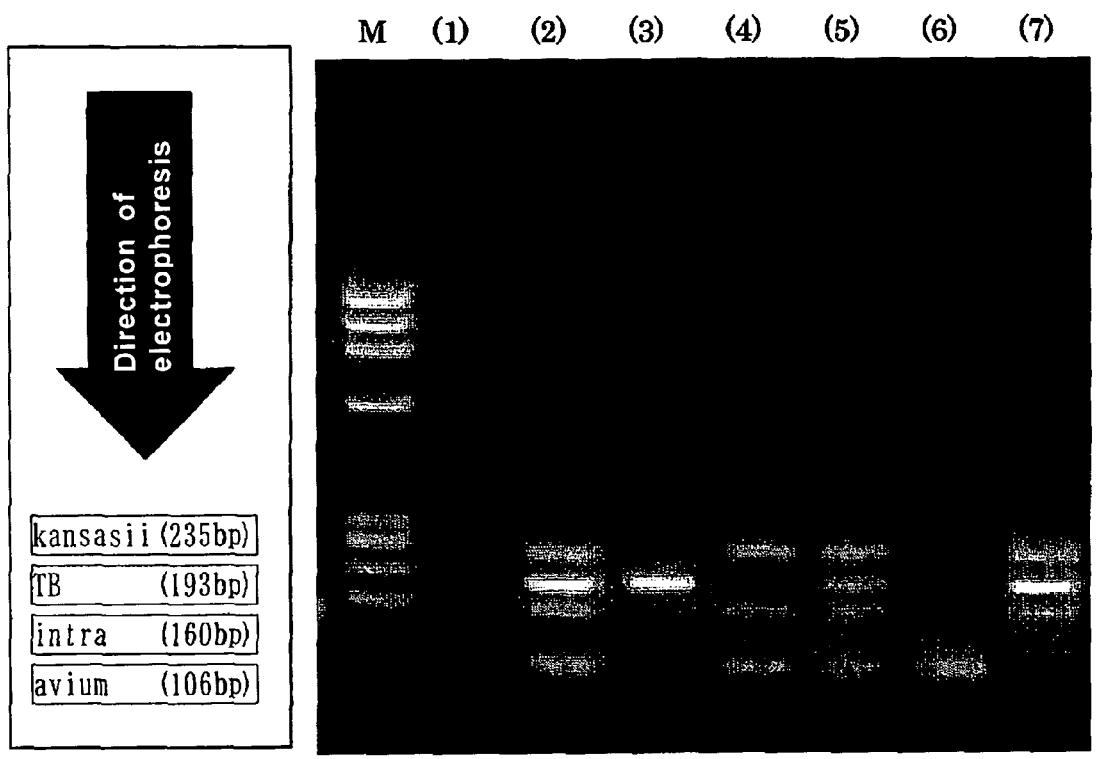

[Fig.6]
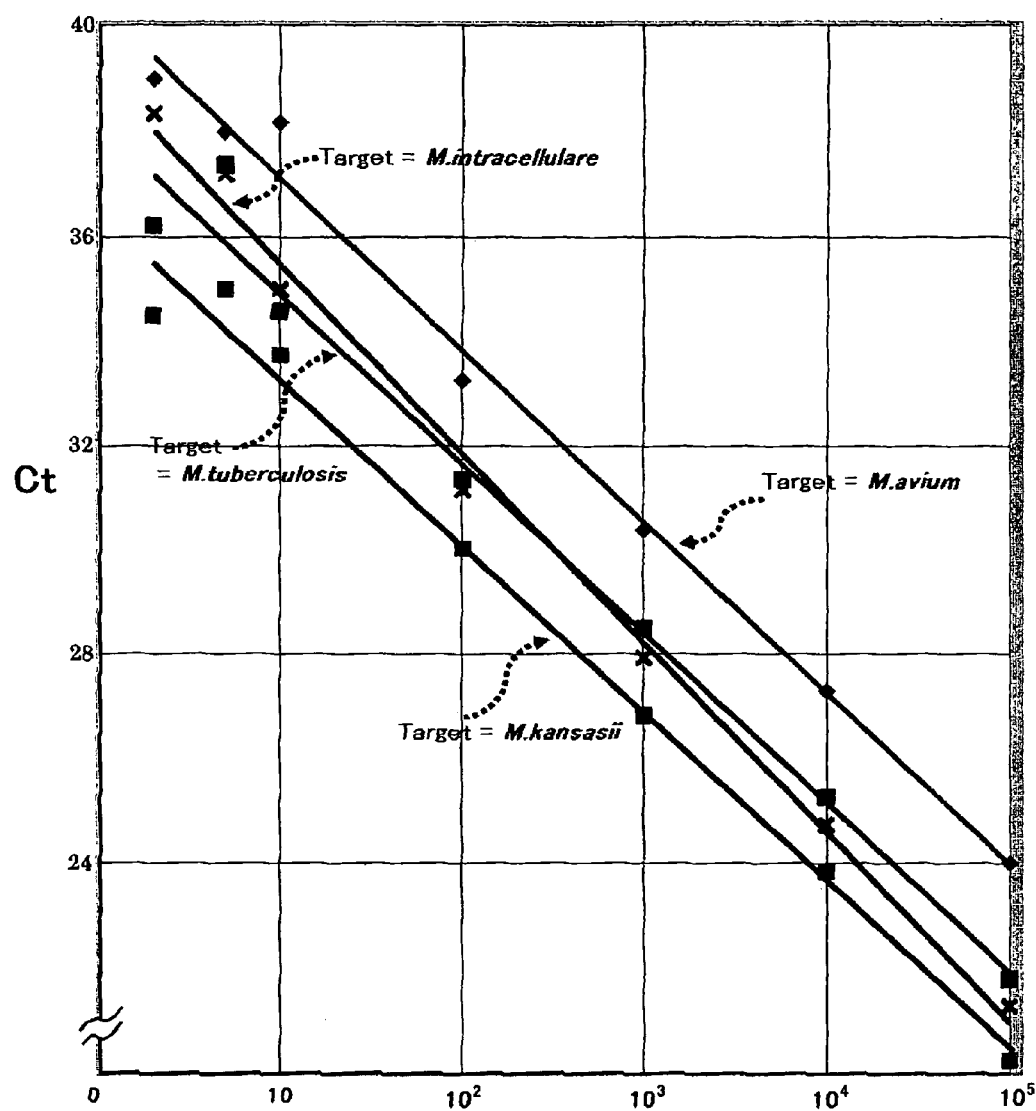

US 8,044,184 B2

PROBE AND PRIMER FOR TUBERCLE BACILLUS DETECTION, AND METHOD OF DETECTING HUMAN TUBERCLE BACILLUS THEREWITH

TECHNICAL FIELD

The present invention relates to a method for detecting human tubercle bacillus, that is, *Mycobacterium tuberculosis* (hereinafter designates as *Mycobacterium* tuberculosis), in laboratory tests by utilizing an amplification of the nucleic acid and a detection system thereof.

BACKGROUND ART

*Mycobacterium tuberculosis* is a pathogenic microbe causing tuberculosis in human, and is Gram-positive bacillus belonging to genus *Mycobacterium* having acidophilic properties. In spite of the significant decrease of tuberculosis in recent years, it has recently become serious problems due to increased the incidence rate in elderly and the outbreak of the group infection in the young people who are not experienced tuberculous infection.

On the other hand, it is also known that besides *Mycobacterium tuberculosis*, non-tuberculous *Mycobacteria* such as *Mycobacterium avium, Mycobacterium intracellulare* and *Mycobacterium kansasii* also exhibit pathogenicity for human. Further, it has also become a big problem for non-tuberculous *Mycobacteria* to develop disease in patients infected with AIDS virus. Since most of these non-tuberculosis Mycobacteriosis exhibit resistance against antituberculous agents, differential diagnosis between tuberculosis and non-tuberculosis mycobacteriosis becomes important for determining therapeutic strategy. However, since differentiation from tuberculosis based on clinical symptom and histopathological observation is quite difficult, the diagnosis has to be determined by using identification of bacteria.

When the differential diagnosis is made between the tuberculosis and the non-tuberculosis mycobacteriosis, the specimens are generally separately cultured in the Ogawa medium, and then subjected to biochemical tests for the identification of the species. However, since growth of genus *Mycobacterium* is generally slow, a considerable time has to be required for the culture. For that reason, when the conventional fundamental tests such as smear examination and culture examination are conducted, the isolation and culture of bacteria for obtaining the diagnostic result to determine tuberculosis or not requires at least for 3 to 4 weeks, and then a time period of further 2 to 3 weeks has to be required for various tests on identification of species.

Although another method for detecting tubercle bacillus using anti-genus *Mycobacterium* antigen antibody is known, specificity to tubercle bacillus is deficient due to cross reaction among species of genus *Mycobacterium*, and as a result, sensitivity is not sufficient.

Recently, a diagnostic technique by applying nucleic acid amplification techniques such as polymerase chain reaction (PCR) has been examined as a useful means, as well as application thereof to the diagnosis of tubercle bacillus. It has been studied whether various regions on DNA genomes of tubercle bacillus can be used as a target for detecting tubercle bacillus using PCR.

For example, a method for detecting genetic region coding the 65 KDa antigen of genus *Mycobacterium* has been reported (refer to, e.g., non-patent document 1, non-patent document 2, non-patent document 3, non-patent document 4, and non-patent document 5). However, it is known that the same genus such as *M. avium, M. fortuitum, M. paratuberculosis, M. kansasii, M. malmoense*, BCG and *M. marinum* as well as *Mycobacterium tuberculosis* have the gene of the 65 kDa antigen is known. Especially, since the 65 kDa antigen has a high cross reactivity with *M. avium* or *M. kansasii* which are the representative causative microorganisms of non-tuberculosis Mycobacteriosis, the method for detecting the gene of 65 kDa antigen has still a problem as a method for specifically detecting *Mycobacterium tuberculosis*.

Further, a test examination for identifying *M. tuberculosis* using a gene sequence coding MPB70 protein, which was identified by DNA of *Mycobacterium bovis*, has been studied (refer to e.g. non-patent document 6). However, Kulski, et al. reported the result in FEMS Microbiol. Lett. 1997 Mar. 1; 148(1): 43-48 (non-patent document 7). Namely, as a result of an examination by PCR, the cross reaction with the similar sequence in DNA of *M. kansasii* was found to occur when MPB70 protein was targeted. Consequently, this method has still a problem as a method for specifically detecting *Mycobacterium tuberculosis*.

Alternatively, a method for detecting *M. tuberculosis/bovis* using a gene sequence coding a protein antigen b (Pab) as a marker has been reported (refer to e.g. non-patent document 8), and usefulness of this marker in using for detecting *M. tuberculosis/bovis* has been confirmed. However, since in the case of Pab gene, only one copy can exist in genome of *M. tuberculosis*, it is considered not so preferable as a material for targeting nucleic acid amplification (contrary to that, in the case of IS6110 sequence described below, ten copies exist in genome of *M. tuberculosis*).

Further, RFLP (Restriction fragment length polymerization) by using IS6110 as a probe was reported to be able to utilize for diagnosis of tubercle bacillus (refer to e.g. non-patent document 9). This sequence has widely been used as an important tool for the epidemiological survey of tuberculosis in many countries in the world. IS6110 is an insertion sequence specific to tubercle bacillus, and exists plurally on the chromosomal DNA, with the different number and location depending on the strain, and this genetic character is inherited stably in some extent. Therefore, different RFLP patterns are shown depending on difference in strain, and grouping based on their origins can be possible. There are many reports on detection method of tubercle bacillus using IS6110, indicating sensitivity exceeding 75% as well as specificity of nearly 100%. However, in the mean time, a study result indicating that there is a possibility to cause false positive in the detection method using IS6110, has also been reported (refer to non-patent document 10). Although there is a detection method performing PCR by designing a primer specific to IS6110 has also been known (refer to e.g. patent document 1, patent document 2, patent document 3 and patent document 4), this method has a problem that sequences relating to IS6110 derived from genus *Mycobacterium* other than *M. tuberculosis* is amplified, too. Further, IS6110-like sequences exist in other microorganism species other than tubercle bacillus, and as a result, it has been suggested that these microorganisms might be detectable by the detection method of targeting IS6110. Consequently, any of the conventional methods for detecting IS6110 has a problem of insufficiency in specifically detecting *Mycobacterium tuberculosis*.

Accordingly, there is a need for establishing a novel method for specifically detecting *Mycobacterium tuberculosis*.

[Patent Document 1]: JP-A-05-507617
[Patent Document 2]: JP-A-11-514522
[Patent Document 3]: JP No. 2814422

[Patent Document 4]: U.S. Pat. No. 5,370,998
[Patent Document 5]: JP-A-60-500717
[Patent Document 6]: JP-A-60-281
[Patent Document 7]: U.S. Pat. No. 5,210,015
[Patent Document 8]: U.S. Pat. No. 5,538,848
[Patent Document 9]: U.S. Pat. No. 5,801,155
[Patent Document 10]: U.S. Pat. No. 5,925,517
[Patent Document 11]: U.S. Pat. No. 6,492,121
[Patent Document 12]: JP No. 2650159
[Patent Document 13]: JP-B-07-114718
[Patent Document 14]: JP-A-58-040099
[Patent Document 15]: JP-A-62-265999
[Non-patent Document 1]: Chia et al., J. Clin. Microbiol., 1990, 28(9), 1877-1880.
[Non-patent Document 2]: Brisson-Noel et al., Lancet, 1989, 334, 1069-1071
[Non-patent Document 3]: Hackel et al, Molecular and cellular Probes, 1990, 4, 205-210.
[Non-patent Document 4]: Woods, Cole, FEMS Microbiology Letters, 1989, 65, 305-310.
[Non-patent Document 5]: Hance et al., Molecular Microbiology, 1989, 3(7), 843-849.
[Non-patent Document 6]: Kulski et al., J. Clin. Microbiol., 1995, 33, 668-674
[Non-patent Document 7]: Kulski et al., FEMS Microbiol. Lett. Mar. 1, 1997, 148(1), 43-48.
[Non-patent Document 8]: Sjobring et al., J. Clin. Microbiol., 1990, 28(10), 2200-2204.
[Non-patent Document 9]: Hermans P W M et al., J. Clin. Microbiol., 1990, 28, 2051-2058.
[Non-patent Document 10]: Lee et al., Neurological Sciences, 1994, 123, 173-179.
[Non-patent document 11]: Thierry et al., Nucleic acid Res., 1990, 18(1), 188.
[Non-patent Document 12]: Nucleic acids Res., 1986, 14, 6115-6128.
[Non-patent Document 13]: Kent P T, Kubica G P, Public Health Mycobacteriology, A Guide for the Level III Laboratory, U.S. Department of Health and Human Services, Public Health Service, Center for Disease Control, Atlanta, U.S.A., 1985, p. 31-55.

DISCLOSURE OF THE INVENTION

Problems to be Solved by the Invention

The present invention has been made under the above circumstances, and an object of the present invention is to provide a novel primer for detecting tubercle bacillus without exhibiting false positive test in the diagnosis, and an easy-to-use, rapid and highly precise method for detecting *Mycobacterium tuberculosis* using the same.

Means for Solving Problems

The present invention has been made for solving the above problems, and is constituted by the following items.
(1) An oligonucleotide comprising a part of or an entire sequence of the nucleic acid sequence described in SEQ ID NO: 1, SEQ ID NO:2, SEQ ID NO:3, SEQ ID NO:4, SEQ ID NO:5, SEQ ID NO:6, SEQ ID NO:7 or SEQ ID NO:8 (wherein A represents adenine, C represents cytosine, G represents guanine and T represents thymine, and T in any position may be replaced by uracil (U), and hereinafter the same abbreviations will be used) or a part of or an entire sequence of the complementary sequence thereof, wherein the oligonucleotide has a property of hybridizing with the nucleic acid sequence of IS6110 gene in *Mycobacterium tuberculosis*.
(2) A primer for detecting *Mycobacterium tuberculosis* comprising an oligonucleotide comprising a part of or an entire sequence of the nucleic acid sequence described in SEQ ID NO:1, SEQ ID NO:2, SEQ ID NO:3, SEQ ID NO:4 or SEQ ID NO:5, or a part of or an entire sequence of the complementary sequence thereof, wherein the oligonucleotide has a property of hybridizing with the nucleic acid sequence of IS6110 gene in *Mycobacterium tuberculosis*.
(3) A probe for detecting *Mycobacterium tuberculosis* comprising an oligonucleotide comprising a part of or an entire sequence of the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or a part of or an entire sequence of the complementary sequence thereof, wherein the oligonucleotide has a property of hybridizing with the nucleic acid sequence of IS6110 gene in *Mycobacterium tuberculosis*.
(4) A method for detecting *Mycobacterium tuberculosis*, comprising using an oligonucleotide comprising a part of or an entire sequence of the nucleic acid sequence described in SEQ ID NO: 1, SEQ ID NO:2, SEQ ID NO:3, SEQ ID NO:4 or SEQ ID NO:5, or a part of or an entire sequence of the complementary sequence thereof, wherein the oligonucleotide has a property of hybridizing with the nucleic acid sequence of IS6110 gene in *Mycobacterium tuberculosis*, as a primer or/and a probe.
(5) A kit for detecting *Mycobacterium tuberculosis* comprising an oligonucleotide comprising a part of or an entire sequence of the nucleic acid sequence described in SEQ ID NO: 1, SEQ ID NO:2, SEQ ID NO:3, SEQ ID NO:4 or SEQ ID NO:5, or a part of or an entire sequence of the complementary sequence thereof, wherein the oligonucleotide has a property of hybridizing with the nucleic acid sequence of IS6110 gene in *Mycobacterium tuberculosis*, as a primer or/and a probe.

The inventor of the present invention have continued theoretical verifications and experimental verifications on homologies of various gene sequences identified to date among species including *Mycobacterium tuberculosis* and other organisms, and found existence of a base sequence, which is has a property of hybridizing specifically to a specific region of the IS6110 sequence which is the insertion sequence and repeated sequence in *Mycobacterium tuberculosis*, and the base sequence is useful for detecting *Mycobacterium tuberculosis*.

As a result of extensive studies on the basis of these findings, the inventor have developed an oligonucleotide with specificity for *Mycobacterium tuberculosis* and useful for detecting the same (nucleic acid sequence described in SEQ ID NO: 1, SEQ ID NO:2, SEQ ID NO:3, SEQ ID NO:4, SEQ ID NO:5, SEQ ID NO:6, SEQ ID NO:7 and SEQ ID NO:8), a nucleic acid primer and a labeled probe for detecting *Mycobacterium tuberculosis* utilizing these sequences, and established a method for detecting *Mycobacterium tuberculosis* using the same.

Effects of the Invention

According to the method for detecting *Mycobacterium tuberculosis* of the present invention, the diagnostic false positive reaction can be excluded, and as a result, more specific and precise detection of *Mycobacterium tuberculosis* can be performed, as compared with the conventional methods for detecting *Mycobacterium tuberculosis* with targeting IS6110.

BRIEF DESCRIPTION OF THE DRAWINGS

FIG. 1 shows the results of electrophoresis obtained in Example 1.
In FIG. 1, the number in each lane shows the results obtained by using the following samples, respectively.
M4: Molecular weight marker (Marker 4)
a: *Escherichia coli*
b: *Mycobacterium tuberculosis*
c: *Mycobacterium kansasii*
d: *Mycobacterium marinum*
e: *Mycobacterium simiae*
f: *Mycobacterium scrofulaceum*
g: *Mycobacterium gordonae*
h: *Mycobacterium szulgai*
i: *Mycobacterium avium*
j: *Mycobacterium intracellulare*
k: *Mycobacterium gastri*
l: *Mycobacterium xenopi*
m: *Mycobacterium nonchromogenicum*
n: *Mycobacterium terrae*
o: *Mycobacterium triviale*
p: *Mycobacterium fortuitum*
q: *Mycobacterium chelonei*
r: *Mycobacterium abscessus*
s: *Mycobacterium peregrinum*

FIG. 2 shows the electrophoretograms obtained in Example 2.
In FIG. 2, the number in each lane shows the results obtained by using the following samples, respectively.
M1: Molecular weight marker (Marker 1)
M4: Molecular weight marker (Marker 4)
a: *Escherichia coli*
b: *Mycobacterium tuberculosis*
c: *Mycobacterium kansasii*
d *Mycobacterium marinum*
e *Mycobacterium simiae*
f: *Mycobacterium scrofulaceum*
g: *Mycobacterium gordonae*
h: *Mycobacterium szulgai*
i: *Mycobacterium avium*
j: *Mycobacterium intracellulare*
k: *Mycobacterium gastri*
l: *Mycobacterium xenopi*
m: *Mycobacterium nonchromogenicum*
n: *Mycobacterium terrae*
o: *Mycobacterium triviale*
p: *Mycobacterium fortuitum*
q: *Mycobacterium chelonei*
r: *Mycobacterium abscessus*
s: *Mycobacterium peregrinum*

FIG. 3-1 shows electrophoretograms obtained in Comparative Example 1.
In FIG. 3-1, the number in each lane shows the results obtained by using the following samples, respectively.
A band (m) obtained with the sample of *Mycobacterium nonchromogenicum* is indicated by enclosing with a dotted circle. A band (o) obtained with the sample of *Mycobacterium triviale* is indicated by enclosing with a dotted circle and an arrow.

M1: Molecular weight marker (Marker 1)
M4: Molecular weight marker (Marker 4)
a: *Escherichia coli*
b: *Mycobacterium tuberculosis*
c: *Mycobacterium kansasii*
d: *Mycobacterium marinum*
e: *Mycobacterium simiae*
f: *Mycobacterium scrofulaceum*
g: *Mycobacterium gordonae*
h: *Mycobacterium szulgai*
i: *Mycobacterium avium*
j: *Mycobacterium intracellulare*
k: *Mycobacterium gastri*
l: *Mycobacterium xenopi*
m: *Mycobacterium nonchromogenicum*
n: *Mycobacterium terrae*
o: *Mycobacterium triviale*
p: *Mycobacterium fortuitum*
q: *Mycobacterium chelonei*
r: *Mycobacterium abscessus*
s: *Mycobacterium peregrinum*

FIG. 3-2 shows the nucleic acid sequence listing obtained by purifying and analyzing PCR product of the fraction, which was the fraction obtained by the above electrophoresis of the PCR product using the *Mycobacterium triviale* sample (o), and the fraction was determined to be very similar in the size of the amplified fraction to the positive band of the sample derived from *Mycobacterium tuberculosis*. The sequence of PCR product derived from *Mycobacterium tuberculosis* of the fraction (b) is designated as 1st Nucleotide Sequence, which is shown on the upper part of the sequence listing (SEQ ID NO: 12) for comparison. Further, the sequence of PCR product derived from *Mycobacterium triviale* obtained from the fraction (o) is designated as 2nd Nucleotide Sequence, and is shown in the lower part of this sequence listing (SEQ ID NO: 13).

FIG. 4 shows the result of the real time PCR detection performed in Example 3, which is a calibration curve obtained by plotting the Ct value (y-axis) versus the copy number of the genome in each DNA sample for PCR (x-axis, logarithmic value).

FIG. 5 shows the result of the electrophoresis obtained in Example 4. In FIG. 5, the number in each lane shows the results obtained by using the following samples, respectively.
M: Molecular weight marker
(1) No sample
(2) *Mycobacterium tuberculosis*+*M. avium*+*M. intracellulare*+*M. kansasii*
(3) *Mycobacterium tuberculosis*
(4) *M. avium*+*M. intracellulare*+*M. kansasii*
(5) *Mycobacterium tuberculosis* (10 copies)+*M. avium*+*M. intracellulare*+*M. kansasii*
(6) *M. avium*
(7) *Mycobacterium tuberculosis*+*M. intracellulare*+*M. kansasii*.

Direction of electrophoretic migration is indicated in the left side of the electrophoretic pattern, and the appearance order of the fraction of each amplified product is shown. "TB" indicates *M. tuberculosis;* "avium" indicates *M. avium*; "intra" indicates *M. intracellulare*; and "kansasii" indicates *M. kansasii*.

FIG. 6 shows the result of the real time PCR detection performed in Example 5, which is a calibration curve obtained by plotting the Ct value (y-axis).versus the copy number of the genome in each DNA sample for PCR (x-axis, logarithmic value)

BEST MODE FOR CARRYING OUT THE INVENTION

IS6110 gene in *Mycobacterium tuberculosis* of the present invention consists of a base sequence with full length of 885 base pairs, and the total base sequence thereof is described, for example, in the paper reported by Pasteur Institute, "Nucleic acid Res. 1990, 18(1): p. 188" (non-patent document 11).

The oligonucleotide of the present invention includes an oligonucleotide comprising a part of or an entire sequence of nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or a part of or an entire sequence of the complementary sequence thereof, wherein the oligonucleotide has a property of hybridizing with the nucleic acid sequence of IS6110 gene in *Mycobacterium tuberculosis* (hereinafter designates as an oligonucleotide of the present invention).

The oligonucleotide comprising a part of or an entire sequence of the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8 of the present invention includes, for example, an oligonucleotide comprising a base sequence sharing about 70% or more, preferably about 80% or more, more preferably about 90% or more, and furthermore preferably about 95% or more of homology with the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or an oligonucleotide comprising a part of or an entire sequence of the nucleic acid sequence described in SEQ ID NO: 1, SEQ ID NO:2, SEQ ID NO:3, SEQ ID NO:4, SEQ ID NO:5, SEQ ID NO:6, SEQ ID NO:7 or SEQ ID NO:8 of the sequence listing, and consisting of continued 10 or more bases, preferably 20 or more bases.

The oligonucleotide comprising a part of or an entire sequence of the complimentary sequence to a part of or an entire sequence of the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8 of the present invention includes, for example, an oligonucleotide comprising a part of or an entire sequence of the nucleic acid sequence having a property of hybridizing with the oligonucleotide comprising a part of or an entire sequence of the nucleic acid sequence described in SEQ ID NO: 1, SEQ ID NO:2, SEQ ID NO:3, SEQ ID NO:4, SEQ ID NO:5, SEQ ID NO:6, SEQ ID NO:7 or SEQ ID NO:8 of the present invention, and the like.

The above-described oligonucleotide comprising a part of or an entire sequence of the nucleic acid sequence having a property of hybridizing with the oligonucleotide comprising a part of or an entire sequence of the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8 of the present invention includes, specifically, an oligonucleotide comprising a part of or an entire sequence of the nucleic acid sequence having a property of hybridizing under a high stringent condition or a stringent condition with the oligonucleotide comprising a part of or an entire sequence of the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8 of the present invention.

In this connection, the "high stringent condition" means a condition of the hybridization in 50% formamide at 42 to 70° C., preferably at 60 to 70° C., followed by washing with 0.1% sodium dodecyl sulfate (SDS) at 25 to 70° C. in 0.2 to 2×SSC.

In addition, the "stringent condition" means specifically, for example, a condition in which the hybridization is performed at 50 to 70° C. for 16 hours in the hybridization solution of 6×SSC or equivalent salt concentration thereof and the hybridized product is washed with 1×SSC or equivalent salt concentration thereof, if necessary after preliminarily washing with the solution of 6×SSC or equivalent salt concentration thereof.

The oligonucleotide having a property of hybridizing with the nucleic acid sequence of IS6110 gene in *Mycobacterium tuberculosis* of the present invention includes an oligonucleotide comprising a nucleic acid sequence having a property of hybridizing under a high stringent condition or a stringent condition with the nucleic acid sequence of IS6110 gene in *Mycobacterium tuberculosis* described hereinbefore, and the like. The high stringent condition or the stringent condition is as described hereinbefore.

The oligonucleotide of the present invention can be deoxyribonucleic acid (DNA) or ribonucleic acid (RNA). In the ribonucleic acid, thymidine residue (T) should naturally be replaced to read as uridine residue (U). DNA can be the DNA containing uridine residue wherein T at any position is replaced with U in the synthesis. RNA can be the RNA containing thymidine residue wherein U at any position is replaced with T in the synthesis, too. Further, one or plural nucleotide can be deleted, inserted or substituted, or modified nucleotide such as inosine (I) can be contained.

In order to obtain the oligonucleotide of the present invention, the oligonucleotide prepared by the publicly known chemical synthesis can be used. Consequently, the oligonucleotide of the same quality can be obtained easily, in large quantity and at a low price, as compared with a cloning method for obtaining an oligonucleotide or a polynucleotide.

For example, the objective oligonucleotide of the present invention can be obtained by using DNA synthesizer performed conventionally in DNA synthesis, synthesizing the oligonucleotide by the conventional phosphoamidite method, and purifying using anion exchange column chromatography.

The primer for detecting *Mycobacterium tuberculosis* of the present invention (hereinafter designates as the primer of the present invention) includes a primer for detecting *Mycobacterium tuberculosis* comprising the oligonucleotide comprising a part of or an entire sequence of the nucleic acid sequence described in SEQ ID NO: 1, SEQ ID NO:2, SEQ ID NO:3, SEQ ID NO:4 or SEQ ID NO:5, or a part of or an entire sequence of the complementary sequence thereof, wherein the oligonucleotide has a property of hybridizing with the nucleic acid sequence of IS6110 gene in *Mycobacterium tuberculosis*.

Specific example of the oligonucleotide comprising a part of or an entire sequence of the nucleic acid sequence described in SEQ ID NO: 1, SEQ ID NO: 2, SEQ ID NO: 3, SEQ ID NO: 4 or SEQ ID NO: 5, or a part of or an entire sequence of the complementary sequence thereof, wherein the oligonucleotide has a property of hybridizing with the nucleic acid sequence of IS6110 gene in *Mycobacterium tuberculosis* used in the primer of the present invention is as described in the explanation of the oligonucleotide of the present invention described hereinbefore.

Further, the primer of the present invention can be used in an appropriate region and an appropriate length selected from the oligonucleotide comprising a part of or an entire sequence of the nucleic acid sequence described in SEQ ID NO: 1 to SEQ ID NO:5, or the oligonucleotide comprising a part of or an entire sequence of the complimentary sequence thereof, in conformity with the objective condition of hybridization of the nucleic acid, and in consideration with dissociation temperature (Tm value). It is preferably be a length with 10 or more bases, more preferably 20 or more bases, which are thought to be a necessary number of bases for maintaining specificity as the primer sequence.

In an example of the primer of the present invention for use in PCR, etc, for example, the forward primer is preferably an oligonucleotide comprising a part of or an entire sequence of the nucleic acid sequence described in SEQ ID NO: 1 or SEQ ID NO:2, or a part of or an entire sequence of the complementary sequence thereof; and the reverse primer is preferably an oligonucleotide comprising a part of or an entire sequence of the nucleic acid sequence described in SEQ ID NO:3 or SEQ ID NO:4, or a part of or an entire sequence of the complementary sequence thereof.

Among them, the forward primer is preferably an oligonucleotide of which the nucleic acid sequence is described in SEQ ID NO: 1 or SEQ ID NO:2, and the reverse primer is preferably an oligonucleotide of which the nucleic acid sequence is described in SEQ ID NO:3 or SEQ ID NO:4.

Particularly preferable combination of the primers includes: (a) a combination of the forward primer which is an oligonucleotide of the nucleic acid sequence described in SEQ ID NO: 1 and the reverse primer which is an oligonucleotide of the nucleic acid sequence described in SEQ ID NO:3; or (b) a combination of the forward primer which is an oligonucleotide of the nucleic acid sequence described in SEQ ID NO:2 and the reverse primer which is an oligonucleotide of the nucleic acid sequence described in SEQ ID NO:4.

A method for obtaining the primer of the present invention is as described in the method for obtaining the nucleotide of the present invention hereinbefore.

The primer of the present invention may be labeled with a labeling substance.

Examples of the labeling substance used for labeling the primer of the present invention with the labeling substance can be any known labeling substance such as a radioisotope, an enzyme, a fluorescent substance, a luminescent substance and a biotin.

For example, the radioisotope includes $^{32}P$, $^{33}P$ and $^{35}S$, etc.; the enzyme includes an alkaline phosphatase, a horseradish peroxidase, etc.; the fluorescent substance includes cyanine dye series such as Cy3 and Cy5 (Amersham Bioscience Inc.), a fluorescein, etc.; and the luminescent substance includes chemiluminescence reagents including an acridinium ester, etc.

A method for labeling the primer of the present invention with the radioisotope includes a method of labeling the primer by incorporating a radioisotope-labeled nucleotide in a synthesis of the primer, or a method of labeling with the radioisotope after synthesis of the primer. Specifically, the method includes commonly used random primer method, nick translation method, a labeling method of 5'-terminal by using T4 polynucleotide kinase, a labeling method of 3'-terminal using a terminal deoxynucleotidyl transferase, and RNA labeling method, etc.

In case of labeling the primer of the present invention with the enzyme, a direct labeling method which is a conventional in this field can be used, and the method includes, for example, a method for binding an enzyme molecule such as alkaline phosphatase and horse radish peroxidase to the primer to be labeled directly by covalent bond.

In case of labeling the primer with the fluorescent substance, for example, a fluorescein-labeled nucleotide can be incorporated into the primer by the conventional labeling method in this field. The nucleotide can be labeled with the fluorescent substance by the method for substituting the nucleotide having a linker arm as a member in the sequence of the oligonucleotide (refer to e.g. non-patent document 12). In this case, a method that uridine having a linker arm at 5-position is chemically synthesized from deoxyuridine by the synthetic method disclosed in JP-A-60-500717 (patent document 5) to introduce the fluorescent substance into the above described oligonucleotide chain, can also be used.

A method for labeling the primer with the luminescent substance and a method for labeling the primer with a biotin can be made by a conventional method for labeling a nucleotide with a luminescent substance or a biotin.

The probe for detecting *Mycobacterium tuberculosis* of the present invention (hereinafter designates as the probe of the present invention) includes a probe comprising an oligonucleotide comprising a part of or an entire sequence of the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or a part of or an entire sequence of the complementary sequence thereof, wherein the oligonucleotide has a property of hybridizing with the nucleic acid sequence of IS6110 gene in *Mycobacterium tuberculosis* (the oligonucleotide of the present invention).

Specific example of the oligonucleotide of the present invention used in the probe of the present invention is as described in the explanation of the oligonucleotide of the present invention described hereinbefore.

The probe of the present invention can be used in an appropriate region and an appropriate length selected from the oligonucleotide comprising a part of or an entire sequence of the nucleic acid sequence described in SEQ ID NO: 1 to SEQ ID NO:8, or the oligonucleotide comprising a part of or an entire sequence of the complimentary sequence thereof, in conformity with the objective condition of hybridization of the nucleic acid, and by calculating dissociation temperature (Tm value). However, if sufficient specificity is made to give the probe, it is preferably be a length with 10 or more bases, more preferably 20 or more bases, which are thought to be a necessary number of base for maintaining specificity as the probe sequence.

In addition, the nucleic acid sequence described in SEQ ID NO:6, SEQ ID NO:7 or SEQ ID NO:8 is a nucleic acid sequence amplified by PCR using the primer of the present invention. For example, the nucleic acid sequence described in SEQ ID NO:6 is a sequence amplified by PCR using the oligonucleotide of the nucleic acid sequence described in SEQ ID NO: 1 as the forward primer and the oligonucleotide of the nucleic acid sequence described in SEQ ID NO:3 as the reverse primer. The nucleic acid sequence described in SEQ ID NO:7 is a sequence amplified by PCR using the oligonucleotide of the nucleic acid sequence described in SEQ ID NO:2 as the forward primer, and the oligonucleotide of the nucleic acid sequence described in SEQ ID NO:4 as the reverse primer. And the nucleic acid sequence described in SEQ ID NO:8 is a sequence amplified by PCR using the oligonucleotide, which is the complimentary sequence of the nucleic acid sequence described in SEQ ID NO:4, (SEQ ID NO: 14) as the forward primer and the oligonucleotide of the nucleic acid sequence described in SEQ ID NO:5 as the reverse primer.

A method for obtaining the probe of the present invention is as described in the method for obtaining the nucleotide of the present invention hereinbefore.

The probe of the present invention may be labeled with a labeling substance.

Examples of the labeling substance used for labeling the probe of the present invention with the labeling substance can be any known labeling substance such as a radioisotope, an enzyme, a fluorescent substance, a luminescent substance and a biotin.

Specific example of the labeling substance for labeling the probe of the present invention and a method for labeling the probe are same as described in the explanation of the method for labeling the primer of the present invention.

Further, the labeled probe used in the real time PCR detection method described hereinbelow includes the probe of the present invention labeled with a conventionally used labeling substance in the real time detection method. For example, the oligonucleotide of the present invention, in which 5'-terminal is labeled with a reporter fluorescent substance (carboxyfluorescein (FAM), hexachlorofluorescein (HEX), tetrachlorofluorescein (TET), and the like), and 3'-terminal is labeled with a quencher dye (e.g. fluorescent substance such as carboxytetramethyl rhodamine (TAMRA), non-fluorescent substance such as Black Hole quencher pigment (BHQ), and 4-((4-(dimethylamino) phenyl) azo) benzoic acid (DABCYL)), can be mentioned.

Specimens used for detection of Mycobacterium tuberculosis of the present invention are various clinical specimens such as human sputum, blood, and transbronchial aspiration. Further, isolated and cultured bacterial cells, a nucleic acid isolated and purified therefrom, or a nucleic acid amplified by the nucleic acid amplification and detection system can be used as a specimen (sample).

Extraction and purification of DNA from the above specimens can be made by the conventional method used in the acid-fact bacterium (tubercle bacillus) DNA extraction.

For example, when a sample of bacterial cells is used, for example, a method in which the bacterial cells are treated with a surface active agent such as SDS or a protein denaturant such as guanidine thiocyanate (GTC) to decompose the membrane structure of the tubercle bacillus, or a method of a physical disruption of the bacterial cells by using glass beads, can be used.

When sputum is used as a specimen, homogenization of the specimen by means of NALC (N-acetyl-L-cysteine)-NaOH method (non-patent document 13) as a preliminary treatment recommended by the US Centers for Disease Control and Prevention (abbreviated as CDC) may preferably be performed.

Then the extraction and purification of DNA can be performed by using the common preparation method of DNA (phenol-chloroform extraction, ethanol precipitation method, etc. "Rapid and simple method for purification of nucleic acids", J. Clin. Microbiol., 1990, March: 28(3), 495-503, Boom R., Sol C J, Salimans M M, Jansen C L, Wertheim-van Dillen P M, van der Noordaa J).

A case, in which cultured bacterial cells isolated from the specimen and cultured are used as a sample for detecting Mycobacterium tuberculosis, is explained as an example. After collecting colonies on the Ogawa medium, suspending the colony in sterilized distilled water and then collecting the bacterial cells by centrifugation. The bacterial cells are resuspended in the distilled water and treated in an autoclave. The bacterial cells are disrupted (for example, by physical disruption using glass beads) and centrifuged to collect the supernatant. DNA can be extracted from the obtained supernatant by purification. Since various kits for the extraction and purification of DNA are commercially available, such kits can be used, or alternatively, the conventional methods (e.g. phenol-chloroform extraction method, precipitation method using ethanol, isopropanol, etc.) can be applied. For example, Genomic-tip (kit for DNA extraction and purification, ion-exchange resin type, QIAGEN Inc.) can be used for extraction and purification of DNA.

The method for detecting Mycobacterium tuberculosis of the present invention includes a method for detecting Mycobacterium tuberculosis comprising using an oligonucleotide comprising a part of or an entire sequence of the nucleic acid sequence described in SEQ ID NO:1, SEQ ID NO:2, SEQ ID NO:3, SEQ ID NO:4 or SEQ ID NO:5, or a part of or an entire sequence of the complementary sequence thereof, wherein the oligonucleotide has a property of hybridizing with the nucleic acid sequence of IS6110 gene in Mycobacterium tuberculosis, as a primer or/and a probe (a method using primer and/or probe of the present invention).

Since the sequence of the specific region of IS6110 nucleic acid sequence in Mycobacterium tuberculosis can be amplified by hybridizing the nucleic acid in the sample with the primer of the present invention, and then performing the primer extension by conducting the nucleic acid amplification using DNA polymerase (e.g. PCR; patent document 6), Mycobacterium tuberculosis can be detected by measuring the primer extension product.

Specific example of the method for detecting Mycobacterium tuberculosis of the present invention using the primer of the present invention includes:

"A method for detecting Mycobacterium tuberculosis characterized by comprising the following steps:
(1) performing PCR using as a primer an oligonucleotide comprising a part of or an entire sequence of the nucleic acid sequence described in SEQ ID NO: 1, SEQ ID NO:2, SEQ ID NO:3, SEQ ID NO:4 or SEQ ID NO:5, or a part of or an entire sequence of the complementary sequence thereof, wherein the oligonucleotide has a property of hybridizing with the nucleic acid sequence of IS6110 gene in Mycobacterium tuberculosis, and a nucleic acid in a sample as a template; and
(2) performing electrophoresis of the primer extension product obtained in the above (1), and determining the existence of Mycobacterium tuberculosis on the bases of the obtained result."

Specific example of the primer of the present invention used in the above method is as described hereinbefore.

Preferable example of the forward primer is an oligonucleotide comprising a part of or an entire sequence of the nucleic acid sequence described in SEQ ID NO: 1 or SEQ ID NO:2, or a part of or an entire sequence of the complementary sequence thereof, wherein the oligonucleotide has a property of hybridizing with the nucleic acid sequence of IS6110 gene in Mycobacterium tuberculosis, and the reverse primer is an oligonucleotide comprising a part of or an entire sequence of the nucleic acid sequence described in SEQ ID NO:3 or SEQ ID NO:4, or a part of or an entire sequence of the complementary sequence thereof, wherein the oligonucleotide has a property of hybridizing with the nucleic acid sequence in IS6110 gene of Mycobacterium tuberculosis.

Conditions and operational methods of the PCR using the above-described primer and the electrophoresis subsequently performed can be those according to the conventional method in this field.

The method for determining existence of Mycobacterium tuberculosis from the result obtained by the electrophoresis includes, for example, (a) a method for detecting by confirming a fraction of the primer extension product having objective base pair number, (b) a method for detecting by hybridizing using the labeled probe, etc.

The method for detecting by confirming a fraction of the primer extension product having objective base pair number of the above (a) includes, for example, a method for detection comprising after performing PCR using the oligonucleotide described in SEC ID NO: 1 as the forward primer and using the oligonucleotide described in SEC ID NO:3 as the reverse primer, performing electrophoresis of the obtained primer extension product, and determining the sample as a positive sample by confirming to contain a fraction of 178 base pairs.

Further, a method for detection comprising after performing PCR using the oligonucleotide described in SEC ID NO:2 as the forward primer and using the oligonucleotide described in SEC ID NO:4 as the reverse primer, then performing electrophoresis of the obtained primer extension product, and determining the sample as a positive sample by confirming a fraction of 182 base pairs, can also be performed Further, a method for detection comprising after performing PCR using the oligonucleotide described in SEC ID NO:14 as the forward primer and using the oligonucleotide described in SEC ID NO:5 as the reverse primer; performing electrophoresis of the obtained primer extension product, and determining the sample as a positive sample by confirming a fraction of 324 base pairs can also be performed.

The method for detection by hybridization using the labeled probe of the above (b) includes a method for detection comprising after performing the electrophoresis, hybridizing the obtained electrophoretic fraction with the labeled probe which is the oligonucleotide of the present invention labeled with the labeling substance, detecting the labeling substance of the labeled probe, and determining the sample as a positive sample by confirming a fraction hybridized with the labeled probe.

For example, in the case when PCR is performed by using the oligonucleotide described in SEQ ID NO: 1 as the forward primer and the oligonucleotide described in SEQ ID NO:3 as the reverse primer, a method for detection comprising after performing PCR, performing electrophoresis, hybridizing the obtained electrophoretic fraction with the labeled probe which is the oligonucleotide comprising the nucleic acid sequence described in SEQ ID NO:6 and is labeled with a labeling substance, detecting the labeling substance of the labeled probe, and determining the sample as a positive sample by confirming a fraction hybridized with the labeled probe, can be performed.

Further, in the case when PCR is performed by using the oligonucleotide described in SEQ ID NO:2 as the forward primer and the oligonucleotide described in SEQ ID NO:4 as the reverse primer, a method for detection comprising after performing PCR, performing electrophoresis, hybridizing the obtained electrophoretic fraction with the labeled probe which is the oligonucleotide comprising the nucleic acid sequence described in SEQ ID NO:7 and is labeled with a labeling substance, detecting the labeling substance of the labeled probe, and determining the sample as a positive sample by confirming a fraction hybridized with the labeled probe, can be performed.

Further, in the case when PCR is performed by using the oligonucleotide described in SEQ ID NO:14 as the forward primer and the oligonucleotide described in SEQ ID NO:5 as the reverse primer, a method for detection comprising after performing PCR, performing electrophoresis, hybridizing the obtained electrophoretic fraction with the labeled probe which is the oligonucleotide comprising the nucleic acid sequence described in SEQ ID NO:8 and is labeled with a labeling substance, detecting the labeling substance of the labeled probe, and determining the sample as a positive sample by confirming a fraction hybridized with the labeled probe, can be performed.

One embodiment of the method for detecting *Mycobacterium tuberculosis* of the present invention will be explained in detail hereinbelow. This is a case of detecting by confirming a fraction of the primer extension product having objective base pair number on the obtained electrophoretic fraction after performing PCR using the oligonucleotide described in SEQ ID NO:2 as the forward primer and the oligonucleotide described in SEQ ID NO:4 as the reverse primer and electrophoresis.

Firstly, in accordance with the method described hereinbefore, purified DNA sample is obtained from the specimen from which *Mycobacterium tuberculosis* to be detected. Separately, an oligonucleotide having the sequence described in SEC ID NO:2 (hereinafter designates as IS_F6) and an oligonucleotide having the sequence described in SEC ID NO:4 (hereinafter designates as IS_R6) which are selected from the nucleotide of the present invention are synthesized by phosphoamidite method using a DNA synthesizer according to the method described hereinbefore.

As a reaction solution for PCR, 10 mM of Tris-HCl buffer solution (pH 8.9) containing 0.2 to 2.0 µM each of IS_F6 and IS_R6, 1.0 to 4.0 mM of $MgCl_2$, 80 mM of KCl, 500 µg/mL of BSA, 0.1% of sodium cholate, 0.005 to 0.2% of Triton X-100 (polyoxyethylene octylphenyl ether, Trade Name, Rohm and Haas Co.), 0.1 to 0.6 mM each of dATP, dCTP, dGTP and dTTP, and 10 to 80 units/mL of Taq DNA polymerase is prepared.

A solution obtained by adding 1 ng of purified DNA sample to the reaction solution for PCR is used as a sample for PCR, and 20 to 40 cycles of PCR are performed with DNA Thermal Cycler. The 5 µL of the reaction solution obtained by the PCR is subjected to electrophoresis using 1.5% agarose gel. Subsequently, after treatment with ethidium bromide staining, ultraviolet induced fluorescence is detected. The molecular weight marker is electrophoreses simultaneously together with the reaction solution, and the length of the detected DNA fragment is calculated by comparing with the relative migration rate. DNA fragment of 182 base pairs (SEQ ID NO:7) in the nucleic acid sequence of IS6110 is predicted to be amplified as a result of PCR using IS_F6 as the forward primer and IS_R6 as the reverse primer. Consequently, a sample which is confirmed the fluorescent band corresponding to 182 base pairs can be determined to be positive.

Another embodiment of the detection method for *Mycobacterium tuberculosis* using the oligonucleotide of the present invention as a primer is shown as follows. That is, PCR is performed using the labeled primer which is the labeled oligonucleotide of the present invention by the labeling method described hereinbefore and using the nucleic acid in the sample as a template, the amount of the labeling substance of the obtained primer extension product is measured. When the labeling substance can be detected, the sample is determined to be positive in *Mycobacterium tuberculosis*.

In the above method, after performing the PCR, the free labeled primer is removed and the amount of the labeling substance of the primer extension product is measured. When the labeling substance can be detected, the sample is determined to be positive in *Mycobacterium tuberculosis*.

A method for removing the free labeled primer includes, for example, following process. That is, the primer extension product in the reaction mixture obtained by performing the PCR reaction is precipitated by the conventional method for precipitating nucleic acid (ethanol precipitation method, precipitation method using isopropanol, etc.), and then the supernatant containing non-precipitated free labeled primer is removed.

Further, a method of separating the primer extension product and the free labeled primer by treating the reaction product obtained by the PCR reaction with gel-chromatography under an appropriate condition, and also a method of separating by electrophoresis, can be mentioned.

In the method for detecting *Mycobacterium tuberculosis* of the present invention, a real time amplification detection system (refer to description of e.g. patent document 7 and patent document 8) can also be performed.

As an example of the detection system by means of the real time amplification detection system, for example, the real time PCR detection system can be mentioned.

Various real time PCR detection method can be used for the detection method of *Mycobacterium tuberculosis* of the present invention, for example, TaqMan™ real time PCR method (refer to e.g. description of patent document 8), MGB Eclipse Probe System method (refer to e.g. description of patent document 9), Molecular Beacons Probe Technology method (refer to e.g. description of patent document 10), LUX Fluorogenic Primer method (Invitrogen Corporation), and Quenching probe-PCR (QP) method (refer to e.g. description of patent document 11).

More specifically, the objective trace amount of DNA can be detected quantitatively and in high sensitively by means of TagMan™ real time PCR method using the probe labeled with FAM at the 5'-terminal and TAMRA at the 3'-terminal (refer to e.g. description of patent document 8).

Namely, the method comprises performing the PCR using the nucleic acid in the sample as a template, and using an oligonucleotide comprising a part of or an entire sequence of the nucleic acid sequence described in SEQ ID NO: 1, SEQ ID NO:2, SEQ ID NO:3, SEQ ID NO:4 or SEQ ID NO:5, or a part of or an entire sequence of the complementary sequence thereof, wherein the oligonucleotide has a property of hybridizing with the nucleic acid sequence of IS6110 gene in *Mycobacterium tuberculosis* as a primer (the primer of the present invention), and using an oligonucleotide comprising a part of or an entire sequence of the nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or a part of or an entire sequence of the complementary sequence thereof, wherein the oligonucleotide has a property of hybridizing with the nucleic acid sequence of IS6110 gene in *Mycobacterium tuberculosis* (the oligonucleotide of the present invention), in which the 5'-terminal is labeled with a reporter fluorescent dye and the 3'-terminal is labeled with a quencher dye as the labeled probe, thereby detecting the labeling substance liberated from the labeled probe.

The principle of the above TagMan™ real time PCR method is as follows. An oligonucleotide probe labeled with fluorescent dye (reporter) at the 5'-terminal and quencher dye at the 3'-terminal and having a property of hybridizing to a specific region of the objective gene, is used. In the probe, fluorescence from the reporter is suppressed by the quencher dye under the usual condition. PCR is performed by using Taq DNA polymerase from the outside under the condition that the fluorescence labeled probe is completely hybridized with the objective gene. As a result of progression the extension reaction by an action of Taq DNA polymerase, the fluorescence labeled probe is hydrolyzed from the 5'-terminal by an action of the exonuclease activity, then the reporter dye is liberated to generate fluorescence. In the real time PCR method, the initial amount of template DNA can be exactly quantified by monitoring the fluorescence intensity in real time.

The probe labeled with fluorescent dye (reporter) at the 5'-terminal and quencher dye at the 3'-terminal used in the real time PCR detection system of the present invention may be the probe of the present invention described hereinbefore, or a probe may be designed on the basis of the sequence of such the probe. For example, the sequence described in SEQ ID NO: 11 designed on the basis of the sequence of SEQ ID NO:6 can be used. The reporter fluorescent substance which is used for labeling at the 5'-terminal includes FAM, HEX, TET, etc., and among them, FAM is preferable. The quencher dye which is used for labeling at the 3'-terminal includes fluorescent substance such as TAMRA and non-fluorescent substance such as BHQ and DAVCYL, and among them TAMPA is preferable.

Preferable example of the forward primer used in the real time PCR detection system of the present invention includes an oligonucleotide comprising a part of or an entire sequence of the nucleic acid sequence described in SEQ ID NO: 1 or SEQ ID NO:2, or a part of or an entire sequence of the complementary sequence thereof, wherein the oligonucleotide has a property of hybridizing with the nucleic acid sequence of IS6110 gene in *Mycobacterium tuberculosis*. Preferable example of the reverse primer includes an oligonucleotide comprising a part of or an entire sequence of the nucleic acid sequence described in SEQ ID NO:3 or SEQ ID NO:4, or a part of or an entire sequence of the complementary sequence thereof, wherein the oligonucleotide has a property of hybridizing with the nucleic acid sequence of IS6110 gene in *Mycobacterium tuberculosis*.

Other reagents used in the real time PCR detection system such as deoxyribonucleoside triphosphate (dATP, dCTP, dGTP and dTTP) and DNA polymerase, can be one conventionally used in the real time PCR, and a procedure of the real time PCR can be performed according to the common protocol of the real time PCR except for using the primer and the probe of the present invention.

An illustrative example of the method for detecting *Mycobacterium tuberculosis* according to the real time PCR detection system (TagMan™ real time PCR method) of the present invention will be explained as follows.

Firstly, in accordance with the method described hereinbefore, purified DNA sample is obtained from the specimen from which *Mycobacterium tuberculosis* is to be detected. Separately, an oligonucleotide having the sequence described in SEC ID NO: 1 (IS_F5) and the sequence described in SEC ID NO:3 (IS_R5) are synthesized by the phosphoamidite method using a DNA synthesizer according to the method described hereinbefore.

The sequence for utilizing as the probe (SEQ ID NO:11) is designed from the oligonucleotide sequence of SEQ ID NO:6 which will be amplified by PCR using IS_F5 and IS_R5 as the primer, and the oligonucleotide having this sequence is synthesized. After that, the reporter dye FAM is bound to the 5'-terminal of the oligonucleotide, and the reporter quencher TAMRA is bound to the 3'-terminal of the oligonucleotide, by conventional methods to obtain the fluorescence labeled probe.

The real time PCR is performed by, for example, using IS_F5 prepared hereinabove as the forward primer, and IS_R5 as the reverse primer as follows.

Namely, 10 mM of Tris-HCl buffer solution (pH 8.9) containing 1 µM each of the primer IS_F5 and the primer IS_R5, 100 to 1000 nM of fluorescence labeled probe, 1.0 to 4.0 mM of $MgCl_2$, 80 mM of KCl, 500 µg/mL of BSA, 0.1% of sodium cholate, 0.005 to 0.2% of Triton X-100, 0.2 mM each of dATP, dCTP, dGTP and dTTP, and 10 to 80 units/mL of Taq DNA polymerase is prepared as a reaction solution. A solution obtained by adding 1 ng of purified DNA sample to 20 µL of the reaction solution is used as a sample for PCR. The sample for PCR is added to the 96 well reaction plate, and the real time PCR is performed by using the real time PCR detector specified to TaqMan™ PCR. Reaction is repeated for 30 to 50 cycles, and fluorescence generated from the reporter dye is measured at each cycle.

In determination of *Mycobacterium tuberculosis*, when fluorescence generated from the reporter dye is measured, the sample can be determined to be positive in *Mycobacterium tuberculosis*.

Since a calibration curve can be prepared in the real time PCR method, a number of genome DNA of *Mycobacterium tuberculosis* in the sample (copy number) can be obtained. Further, since the number is in proportional to a number of *Mycobacterium tuberculosis*, a number of *Mycobacterium tuberculosis* in the specimen can be obtained. The calibration curve can be prepared in accordance with the conventional method in the real time PCR method. For example, using the genome DNA sample of *Mycobacterium tuberculosis* having a known copy number, DNA sample for PCR with the concentration (copy number) of dilution series is prepared as a standard. Subsequently, the real time PCR is performed according to the above described method using DNA sample for PCR in each dilution series, and the fluorescence value generated from the reporter dye is measured. Measured value of the measured fluorescence value (Rn, y-axis) versus each cycle number of PCR (x-axis) is plotted in each DNA sample for PCR in each dilution series to prepare an amplification curve. Subsequently, Rn region where the fluorescence value is exponentially amplified is selected, and a threshold line (Th) is drawn. A point crossing Th and the each amplification curve of each DNA sample for PCR is set as threshold cycle (Ct). Subsequently, the Ct (y-axis) value versus the logarithm of copy number of used each DNA sample for PCR (x-axis) is plotted, and the approximated curve obtained to each Ct can be used as a calibration curve.

For quantitatively determining number of genome DNA (copy number) of *Mycobacterium tuberculosis* in the specimen (sample), firstly DNA is isolated and purified from the specimen from which *Mycobacterium tuberculosis* to be detected, and then the real time PCR is performed on the obtained DNA sample, and an amplification curve is prepared by the same method as shown in hereinabove. Ct value crossing the Th obtained from the calibration curve with the amplification curve obtained above is obtained. Such the Ct value is applied to the calibration curve to obtain an amount of genome DNA of *Mycobacterium tuberculosis* in the specimen (copy number in the sample).

Further, the detection method utilizing RNA transcription product can be applied to the nucleic acid amplification process of the present invention. For example, NASBA (nucleic acid sequence based amplification) method (patent document 12) and 3SR (self-sustained sequence replication) method (patent document 13) can be used. Among them, the constant temperature nucleic acid amplification utilizing concerted reaction of reverse transcriptase and RNA polymerase (reaction is performed under condition of concerted reaction with reverse transcriptase and RNA polymerase) is suitable to the automated measurement system.

Further, the method for detecting *Mycobacterium tuberculosis* of the present invention includes a method comprising using an oligonucleotide labeled with a labeling substance comprising a part of or an entire sequence of nucleic acid sequence described in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or a part of or an entire sequence of the complementary sequence thereof, wherein the oligonucleotide has a property of hybridizing with the nucleic acid sequence of IS6110 gene in *Mycobacterium tuberculosis* (the oligonucleotide of the present invention) as a labeled probe, hybridizing the labeled probe with the nucleic acid in the sample, removing the free labeled probe, and detecting the labeling substance of the hybridized complex.

Specifically, for example, (a) a detection method in which the oligonucleotide of the present invention is bound to a solid carrier to use as a capture probe, which is hybridized with the nucleic acid in the sample, thereby the nucleic acid derived from *Mycobacterium tuberculosis* in the sample is immobilized on the solid phase (e.g. refer to description of patent document 15); and (b) a method for performing sandwich assay in which using the capture probe of above (a) and the labeled probe of the present invention, the nucleic acid in the sample is hybridized therewith to form a complex of the capture probe, the nucleic acid derived from *Mycobacterium tuberculosis* and the labeled probe on the solid carrier, to measure the labeling of the labeled probe (e.g. refer to description of patent document 14) can be mentioned. Further, (c) a method in which after hybridization of the nucleic acid in the sample with the labeled probe of the present invention labeled with a biotin, the nucleic acid in the sample is captured by an avidin-bound carrier, can also be used.

As the reagents used for the method for detecting *Mycobacterium tuberculosis* of the present invention, conventionally used reagents in this field, for example, stabilizing agents such as buffering agents and preservatives without inhibiting stability of coexisting reagents and without inhibiting PCR and hybridization reaction can be used. Further, the concentration thereof may preferably be selected from the concentration range conventionally used in this field.

Specific example of buffer solution includes all buffer solutions used in performing conventional PCR and hybridization reaction, and are, for example, Tris buffer, phosphate buffer, veronal buffer, borate buffer, Good's buffer, etc., and pH thereof is not particularly limited and is preferably within a range of pH 5 to 9 in general.

In addition, if necessary, nucleic acid polymerase (DNA polymerase, RNA polymerase, reverse transcriptase, etc.), substrates corresponding to enzymes (dNTP, rNTP, etc.), double strand intercalating agents (ethidium bromide, SYBR™ Green, etc.) or labeling detection substances such as FAM and TAMRA can be used.

Example of a kit for detecting *Mycobacterium tuberculosis* of the present invention includes "a kit for detecting *Mycobacterium tuberculosis* comprising an oligonucleotide comprising a part of or an entire sequence of the nucleic acid sequence described in SEQ ID NO: 1, SEQ ID NO:2, SEQ ID NO:3, SEQ ID NO:4 or SEQ ID NO:5, or a part of or an entire sequence of the complementary sequence thereof, wherein the oligonucleotide has a property of hybridizing with the nucleic acid sequence of IS6110 gene in *Mycobacterium tuberculosis*, as a primer (the primer of the present invention)". The primer can be labeled with a labeling substance.

The above-mentioned kit may comprise the oligonucleotide of the present invention labeled with a labeling substance as a labeled probe.

Further, the above-mentioned kit includes "a kit comprising as constituent reagents: (1) a forward primer which is an oligonucleotide comprising a part of or an entire sequence of the nucleic acid sequence described in SEQ ID NO: 1 or SEQ ID NO:2, or a part of or an entire sequence of the complementary sequence thereof, wherein the oligonucleotide has a property of hybridizing with the nucleic acid sequence of IS6110 gene in *Mycobacterium tuberculosis*; and (2) a reverse primer which is an oligonucleotide comprising a part of or an entire sequence of the nucleic acid sequence described in SEQ ID NO:3 or SEQ ID NO:4, or a part of or an entire sequence of the complementary sequence thereof, wherein the oligonucleotide has a property of hybridizing with the nucleic acid sequence of IS6110 gene in *Mycobacterium tuberculosis*".

The above kit may further comprise the oligonucleotide of the present invention labeled with a labeling substance as a labeled probe.

Further, the above kit includes "a kit for detecting *Mycobacterium tuberculosis* comprising the oligonucleotide of the present invention as a probe". The probe can be labeled with a labeling substance.

Preferable embodiments and specific examples of the constituent reagents constituting these kits are as described hereinbefore.

In addition, the reagent kit for detecting *Mycobacterium tuberculosis* of the present invention can contain, for example, stabilizing agents such as buffer agents and preservatives without inhibiting stability of coexisting reagents and without inhibiting PCR and hybridization reaction. Concentration thereof may be selected from the concentration range conventionally used in this field.

Specific example of buffer solution includes all buffer solutions used in performing conventional PCR and hybridization reaction, and are, for example, Tris buffer, phosphate buffer, veronal buffer, borate buffer, Good's buffer, etc., and pH thereof is not particularly limited and is preferably within a range of pH 5 to 9 in general.

In addition, if necessary, nucleic acid polymerase (DNA polymerase, RNA polymerase, reverse transcriptase, etc.), substrates corresponding to enzymes (dNTP, rNTP, etc.), double strand intercalating agents (ethidium bromide, SYBR™ Green, etc.) or labeling detection substances such as FAM and TAMRA can be contained.

In the following, the present invention is further explained in detail, and the present invention is not limited thereto by any means.

EXAMPLES

Example 1

(1) Synthesis of PCR Primer for Detecting *Mycobacterium tuberculosis*

An oligonucleotide having a sequence described in SEQ ID NO:2 (ACCTCACCTATGTGTCGACC, hereinafter designates as IS_F6) and an oligonucleotide having a sequence described in SEQ ID NO:4 (AACGTCTTTCAGGTCGAGTACG, hereinafter designates as IS_R6) were synthesized according to the phosphoamidite method by using ABI DNA synthesizer Type 392. The synthesis was conducted according to the procedure described in the manual of ABI Inc., and deprotection of each type of the oligonucleotides was performed by the method of heating an aqueous ammonia solution of the oligonucleotide at 55° C. overnight. Subsequently, the synthesized oligonucleotides were purified using anion-exchange column chromatography with HFPLC from Pharmacia Corp.

(2) Preparation of Samples

Using the bacteria shown hereinbelow, DNA was extracted and purified by the following methods to obtain DNA samples. All bacteria were clinical isolates, and their species were already discriminated after cultivation by the colony form, the conventional biochemical tests, etc.

With regard to bacteria belonging to genus *Mycobacterium*, colonies on the Ogawa medium were suspended in purified water, autoclaved (at 120° C. for 20 minutes under 2 atmospheric pressure), then disrupted the bacterial cells (by physical disruption with glass beads, diameter 2 mm), and centrifuged to obtain a supernatant. Extraction and purification of DNA from the obtained supernatant were performed using Genomic-tip (a kit for DNA extraction and purification, ion-exchange resin type, QIAGEN Inc.). With regard to *Escherichia coli*, DNA was extracted and purified according to the conventional DNA extraction method for *Escherichia coli*.

The thus obtained purified DNA was prepared to result final concentration of 1 ng/μL (10 mM Tris-HCl buffer, pH 8.9), and was used as a DNA sample.

a: *Escherichia coli*
b: *Mycobacterium tuberculosis*
c: *Mycobacterium kansasii*
d: *Mycobacterium marinum*
e: *Mycobacterium simiae*
f: *Mycobacterium scrofulaceum*
g: *Mycobacterium gordonae*
h: *Mycobacterium szulgai*
i: *Mycobacterium avium*
j: *Mycobacterium intracellulare*
k: *Mycobacterium gastri*
l: *Mycobacterium xenopi*
m: *Mycobacterium nonchromogenicum*
n: *Mycobacterium terrae*
o: *Mycobacterium triviale*
p: *Mycobacterium fortuitum*
q: *Mycobacterium chelonei*
r: *Mycobacterium abscessus*
s: *Mycobacterium peregrinum*

(3) PCR

IS_F6 prepared in the above (1) was used as the forward primer and IS_R6 prepared in the above (1) was used as the reverse primer, and PCR was performed as follows.

Firstly, 10 mM of Tris-HCl (pH 8.9) buffer containing 1 μM each of the primer IS_F6 and the primer IS_R6, 1.5 mM of $MgCl_2$, 80 mM of KCl, 500 μg/mL of BSA, 0.1% of sodium cholate, 0.1% of Triton X-100 (polyoxyethylene octylphenyl ether, Trade Name, Rohm and Haas Co.), 0.2 mM each of dATP, dCTP, dGTP and dTTP, and 40 units/mL of Taq DNA polymerase (Nippon Gene Co. Ltd.) was prepared as a reaction solution for PCR.

A solution obtained by adding 1 ng of DNA sample to 20 μL of the reaction solution for PCR was used as a sample for PCR, and 30 cycles of PCR were performed with DNA Thermal Cycler (DNA Engine PTC200) from MJ Research under the following reaction conditions.

PCR reaction conditions:
Thermal denaturation: 94° C., 0.5 minute
Annealing: 55° C., 1 minute
Polymerization reaction: 75° C., 0.5 minute (4) Detection The 5 μL of the reaction solution obtained by the PCR in the above (3) was subjected to electrophoresis using 1.5% agarose gel. Electrical condition in the electrophoresis was at constant voltage of 100 V for 30 minutes. Operational method and other conditions were in accordance with generally used method described in "Bio-Experiments Illustrated, Vol. 2, p. 53-63" (by Nakayama Hiroki, Shujunsha Co. Ltd.). Subsequently, after treatment with ethidium bromide staining, ultraviolet induced fluorescence was detected by using UV sample imaging device FAS-III System (Toyobo Co. Ltd.). The molecular weight marker was electrophoresed simultaneously together with the reaction solution, and the length of the detected DNA fraction was calculated by comparing with these relative migration rates. The X174/HaeIII digest (marker 4, Nippon Gene Co. Ltd.) was used as the molecular weight marker.

(5) Results

Thus obtained results by electrophoresis are shown in FIG. 1.

In FIG. 1, the number in each lane shows the results obtained by using the following samples, respectively.
M4: Molecular weight marker (marker 4)
a: *Escherichia coli*
b: *Mycobacterium tuberculosis*
c: *Mycobacterium kansasii*
d: *Mycobacterium marinum*
e: *Mycobacterium simiae*
f: *Mycobacterium scrofulaceum*
g: *Mycobacterium gordonae*
h: *Mycobacterium szulgai*
i: *Mycobacterium avium*
j: *Mycobacterium intracellulare*
k: *Mycobacterium gastri*
l: *Mycobacterium xenopi*
m: *Mycobacterium nonchromogenicum*
n: *Mycobacterium terrae*
o: *Mycobacterium triviale*
p: *Mycobacterium fortuitum*
q: *Mycobacterium chelonei*
r: *Mycobacterium abscessus*
s: *Mycobacterium peregrinum*

DNA fragment of 182 base pairs (SEQ ID NO:7) in the nucleic acid sequence of IS6110 was predicted to be amplified as the result of PCR using the forward primer IS_F6 and the reverse primer IS_R6. Consequently, a sample which is confirmed the fluorescent band corresponding to 182 base pairs was determined to be positive.

As is clear from the results of FIG. 1, as a result of performing PCR using the primer IS-F6 and the primer IS-R6 of the present invention, only when *Mycobacterium tuberculosis* was used as the sample (b), a fluorescent band of 182 base pairs was able to be confirmed and the sample was determined as positive. Contrary to this, when other bacterial species of genus *Mycobacterium* and bacterium of other genus *Escherichia coli* were used as the samples (a and c to s), corresponding fluorescent band could not be confirmed, and accordingly these samples were determined as negative.

From the above results, it is understood that *Mycobacterium tuberculosis* can be specifically detected by using the oligonucleotide of the present invention as the primer in PCR. In addition, since high sensitive detection can be expected by the nucleic acid amplification method such as PCR, isolation process of bacteria is not required and clinical specimens can be used directly for detection. Consequently, the detection of *Mycobacterium tuberculosis*, which requires several weeks for cultivation in the conventional method of detection after culturing bacteria, can be completed within one day at the most.

Example 2

(1) Synthesis of PCR Primer for Detecting *Mycobacterium tuberculosis*

An oligonucleotide having the sequence described in SEQ ID NO:1 (TGGGTAGCAGACCTCACCTAT, hereinafter designates as IS_F5) and an oligonucleotide having the sequence described in SEQ ID NO:3 (CGAGTACGCTTTCTTGTTGG, hereinafter designates as IS_R5) were synthesized by the same method as in Example 1 using the same equipment as in Example 1.

(2) Preparation of Samples

DNA samples obtained in Example 1 (2) were used.

(3) PCR

IS_F5 prepared in the above (1) was used as the forward primer, and IS_R5 prepared in the above (1) was used as the reverse primer, and PCR was performed as described hereinbelow.

Firstly, 10 mM of Tris-HCl (pH 8.9) buffer containing 1 µM each of the primer IS_F5 and the primer IS_R5, 1.5 mM of MgCl$_2$, 80 mM of KCl, 500 µg/mL of BSA, 0.1% of sodium cholate, 0.1% of Triton X-100, 0.2 mM each of dATP, dCTP, dGTP and dTTP, and 40 units/mL of Taq DNA polymerase (Nippon Gene Co. Ltd.) was prepared as the reaction solution for PCR.

A solution obtained by adding 1 ng of DNA sample to 20 µL of the reaction solution for PCR was used as a sample for PCR, and PCR was performed by the same method as in Example 1(3) using the same equipment used in Example 1 (3) under the same reaction conditions.

(4) Detection

Detection was performed by the same method as in Example 1 (4), that is, 1.5% agarose electrophoresis, ethidium bromide staining and detection of ultraviolet induced fluorescence.

(5) Results

Thus obtained results of electrophoresis are shown in FIG. 2.

In FIG. 2, the number in each lane shows the results obtained by using the following samples, respectively.
M4: Molecular weight marker (marker 4)
a: *Escherichia coli*
b: *Mycobacterium tuberculosis*
c: *Mycobacterium kansasii*
d: *Mycobacterium marinum*
e: *Mycobacterium simiae*
f: *Mycobacterium scrofulaceum*
g: *Mycobacterium gordonae*
h: *Mycobacterium szulgai*
i: *Mycobacterium avium*
j: *Mycobacterium intracellulare*
k: *Mycobacterium gastri*
l: *Mycobacterium xenopi*
m: *Mycobacterium nonchromogenicum*
n: *Mycobacterium terrae*
o: *Mycobacterium triviale*
p: *Mycobacterium fortuitum*
q: *Mycobacterium chelonei*
r: *Mycobacterium abscessus*
s: *Mycobacterium peregrinum*

According to the results of PCR using the forward primer IS_F5 and the reverse primer IS_R5, DNA fragment of 178 base pairs (SEQ ID NO:6) in the nucleic acid sequence of IS6110 can be predicted to be amplified. Consequently, a sample which is confirmed a fluorescent band corresponding to 178 base pairs was determined to be positive.

Comparative Example 1

Detection of *Mycobacterium tuberculosis* was performed by a detection method using a primer sequence prepared on the basis of the publicly known IS6110 sequence (JP-A-11-514522, patent document 11).

(1) Synthesis of PCR Primer for Detecting *Mycobacterium tuberculosis*

Among the primer sequences disclosed in JP-A-11-514522, an oligonucleotide having the sequence of "TTCGGACCACCAGCACCTAACC" (SEQ ID NO:9, hereinafter designates as IS_F2) and an oligonucleotide having the sequence of "CCTTCTTGTTGGCGGGTCCAG" (SEQ ID NO:10, hereinafter designates as IS_R2), were synthesized.

Synthesis was performed by the same method as in Example 1(1).

(2) Preparation of Samples

DNA samples obtained in Example 1 (2) were used.

(3) PCR

IS_F2 prepared in the above (1) was used as the forward primer, and IS_R2 prepared in the above (1) was used as the reverse primer, and PCR was performed as described hereinbelow.

Firstly, 10 mM of Tris-HCl (pH 8.9) buffer containing 1 μM each of the primer IS_F2 and the primer IS_R2, 1.5 mM of $MgCl_2$, 80 mM of KCl, 500 pg/mL of BSA, 0.1% of sodium cholate, 0.1% of Triton X-100, 0.2 mM each of dATP, dCTP, dGTP and dTTP, and 40 units/mL of Taq DNA polymerase (Nippon Gene Co. Ltd.) was prepared as the reaction solution for PCR.

A solution obtained by adding 1 ng of DNA sample to 20 μL of the reaction solution for PCR was used as a sample for PCR, and PCR was performed using the same equipment used in Example 1 (3) under the same reaction conditions.

(4) Detection

Detection was performed by the same method as in Example 1 (4), that is, 1.5% agarose electrophoresis, ethidium bromide staining and detection of ultraviolet induced fluorescence. The λ/Hind III digest (marker 1) (lane M1) and X174/Hae III digest (marker 4) (Nippon gene Co. Ltd.) were used as the molecular weight marker.

(5) Results

Thus obtained the results of electrophoresis are shown in FIG. 3-1.

In FIG. 3-1, the number in each lane shows the results obtained by using the following samples, respectively.

M1: Molecular weight marker (marker 1)
M4: Molecular weight marker (marker 4)
a: *Escherichia coli*
b: *Mycobacterium tuberculosis*
c: *Mycobacterium kansasii*
d: *Mycobacterium marinum*
e: *Mycobacterium simiae*
f: *Mycobacterium scrofulaceum*
g: *Mycobacterium gordonae*
h: *Mycobacterium szulgai*
i: *Mycobacterium avium*
j: *Mycobacterium intracellulare*
k: *Mycobacterium gastri*
l: *Mycobacterium xenopi*
m: *Mycobacterium nonchromogenicum*
n: *Mycobacterium terrae*
o: *Mycobacterium triviale*
p: *Mycobacterium fortuitum*
q: *Mycobacterium chelonei*
r: *Mycobacterium abscessus*
s: *Mycobacterium peregrinum*

According to the results of replicate PCR using the forward primer IS_F2 and the reverse primer IS_R2, DNA fragment of 197 base pairs (SEQ ID NO:6) in the nucleic acid sequence of IS6110 was predicted to be amplified. Consequently, a sample which is confirmed fluorescent band corresponding to 197 base pairs was determined to be positive.

As is clear from the results of FIG. 2 obtained in Example 2, as a result of performing PCR using the primer IS_F5 and the primer IS_R5 of the present invention, only when *Mycobacterium tuberculosis* was used as the sample (b), the fluorescent band of 178 base pairs was able to be confirmed and the sample was determined as positive. Contrary to this, when other bacterial species of genus *Mycobacterium* and bacterium of other genus *Escherichia coli* were used as the samples (a and c to s), corresponding fluorescent band could not be confirmed, and accordingly all samples were determined as negative.

Contrary to that, as is clear from the results of FIG. 3-1 obtained in Comparative Example 1, as a result of performing PCR using primer IS_F2 and primer IS_R2 which are publicly know primers, the sample was able to be determined as positive when *Mycobacterium tuberculosis* was used as the sample. However, in other cases, for example, when *Mycobacterium nonchromogenicum* was used as the sample (m) and when *Mycobacterium triviale* was used as the sample (o), apparent bands were observed and these samples were determined as false positive, too. In FIG. 3-1, the band obtained by using the sample of *Mycobacterium nonchromogenicum* (m) is shown in the dotted circle. The band obtained by using the sample of *Mycobacterium triviale* (o) is shown in the dotted circle and indicated by the arrow.

Namely, it is understood that the specific detection of *Mycobacterium tuberculosis* is difficult by the method of Comparative Example 1.

From the results of obtained by electrophoresis in Comparative Example 1, in particular, the result obtained by using the sample of *Mycobacterium triviale* (o) was noted, which was determined to be very similar in the size of the amplified fragment to the positive band of *Mycobacterium tuberculosis*. In FIG. 3-1, the band is specially shown with the arrow. For further analysis on this PCR product, the PCR product in the electrophoresis fraction was cut off and DNA was purified. The sequence thereof was analyzed by PCR-direct sequencing method using Sequence kit of ABI Inc.

The obtained sequence is shown in FIG. 3-2. Among sequences shown in FIG. 3-2, the sequence of PCR product derived from the sample of *Mycobacterium tuberculosis* of the fraction (b) is designated as 1st Nucleotide Sequence, which is shown on the upper part of this sequence listing (SEQ ID NO:12). Further, the sequence of PCR product derived from the sample of *Mycobacterium triviale* obtained from the fraction (o) is designated as 2nd Nucleotide Sequence, and is shown in the lower part of this sequence listing (SEQ ID NO:13).

As a result from sequence analysis of DNA fragment, it is confirmed that this sequence is the nucleic acid sequence derived from *Mycobacterium triviale*, and confirmed to be identical to the nucleic acid sequence of IS6110 specific to *Mycobacterium tuberculosis* only in the sequence region of the primer IS_F2 and the primer IS_R2 used in Comparative Example 1. Consequently, it is understood that when PCR is performed using the publicly known primers IS_F2 and the primer IS_R2, a nucleic acid sequence other than *Mycobacterium tuberculosis* is also amplified, and that thus the primer has an obvious defect in design thereof.

Considering the above, it is understood that judgment of false positive can be excluded, and *Mycobacterium tuberculosis* can be detected specifically and precisely, as compared with the conventional primers and detection method for *Mycobacterium tuberculosis* using the primers, when the detection of *Mycobacterium tuberculosis* is performed by PCR using the oligonucleotide of the present invention as the primer. On this point, the method of the present invention is extremely superior in comparison with the detection method for *Mycobacterium tuberculosis* using the conventional primers.

Example 3

Detection of *Mycobacterium tuberculosis* by Real Time PCR Amplification System (1) Synthesis of PCR Primer for Detecting *Mycobacterium tuberculosis*

Oligonucleotides of IS_F5 and IS_R5 were synthesized by the same method as in Example 1 using the same equipment as in Example 1 (1).

(2) Preparation of Probe for Detecting *Mycobacterium tuberculosis*

A sequence of "ACCGACGCCTACGCTCGCAG" for utilizing as the probe was designed from the oligonucleotide sequence of SEQ ID NO:6 which would be amplified by PCR using IS_F5 and IS_R5 as the primer, and then the oligonucleotide having this sequence was synthesized (hereinafter designates as IS_F5R5_FANTAM, SEQ ID NO:11). The reporter dye FAM was linked to 5'-terminal of this oligonucleotide and the reporter quencher TAMRA was linked to 3'-terminal to obtain a labeled oligonucleotide probe (TaqMan™ fluorescent labeled probe, Applied Biosystems Japan Inc.).

(3) Preparation of DNA Sample for PCR

With regard to the DNA sample obtained from *Mycobacterium tuberculosis* prepared in Example 1 (2), an amount of DNA in the sample was measured by measuring absorbance. Amount of genome DNA (genome copy number) in the sample was determined by comparing the amount of obtained DNA with the known amount of genome DNA of *Mycobacterium tuberculosis*. Genome DNA having $10^8$ copies/μL was obtained.

Subsequently, the DNA sample was diluted to give dilution series of $10^5$, $10^4$, $10^3$, $10^2$, 10, 5, and 2 copies/μL by using 10 mM of Tris-HCl buffer, pH 8.9 to prepare the DNA samples for PCR.

(4) Real Time PCR

The real time PCR was performed by using IS_F5 prepared in (1) hereinabove as the forward primer and IS_R5 prepared in (1) hereinabove as the reverse primer, as follows.

Namely, 10 mM of Tris-HCl buffer (pH 8.9) containing 1 μM each of the primer IS_F5 and the primer IS_R5, 195 nM of fluorescence labeled probe IS_F5R5FAMTAM prepared in the above (1), 1.5 mM of $MgCl_2$, 80 mM of KCl, 500 μg/mL of BSA, 0.1% of sodium cholate, 0.1% of Triton X-100, 0.2 mM each of dATP, dCTP, dGTP and dTTP, and 40 units/mL of Taq DNA polymerase (Nippon Gene Co. Ltd.) was prepared as the reaction solution.

A solution prepared by adding 1 ng of the DNA sample of each dilution series to 20 μL of the reaction solution was used as the sample for PCR. The sample for PCR was added to the well of 96 well reaction plate (MicroAmp Optical 96 well Reaction Plate, Applied Biosystems Japan, Inc.), and the real time PCR was performed by using the Thermal Cycler—Sequence detection System specified to TaqMan™ PCR (ABI7000, Applied Biosystems Japan, Inc.). PCR cycling conditions were 95° C. for 10 minutes for keeping warm, followed by 50 cycles of reaction at 95° C. for 15 seconds and at 60° C. for 1 minute, with the measurement of fluorescence value generated from the reporter dye in each cycle. The fluorescence value was measured on every one plate of the 96 well reaction plate used for the measurement by using the function of Thermal Cycler used in the measurement to digitalize the relative ratio of fluorescence intensity.

(5) Results and Analysis

The calibration curve was prepared according to the conventional method used in the real time PCR. Namely, the fluorescent value generated from the reporter dye (Rn, y-axis) versus each cycle number of PCR (x-axis) is plotted in each DNA sample of PCR to prepare an amplification curve. Subsequently, Rn region, where the fluorescence value was exponentially amplified, was selected and threshold line (Th) was drawn. A point crossing Th and the each fluorescence value of each DNA sample for PCR was set as threshold cycle (Ct). Ct value (y-axis) versus the copy number of genome in each DNA sample for PCR used α-axis, logarithmic value) was plotted, and the approximated curve obtained to each Ct value was used as the calibration curve. The obtained calibration curve is shown in FIG. 4.

$$y=-3.555x+39.13$$

$$R^2=0.996$$

From the above results, since fluorescence was detected in the real time PCR, it is understood that *Mycobacterium tuberculosis* is able to be detected by using the oligonucleotide of the present invention as the primer in PCR, and designing the labeled probe from the sequence of the amplification region, and performing real time PCR.

In addition, since the calibration curve was able to be prepared, it is understood that *Mycobacterium tuberculosis* can be quantitatively determined by applying real time PCR using the primer and the probe of the present invention. Further, it is understood from FIG. 4 that *Mycobacterium tuberculosis* can be detected by the real time PCR using the primer and the probe of the present invention even under the condition in which only two copies of genome DNA from *Mycobacterium tuberculosis* present as the initial level.

Further, when the real time PCR is utilized, an initial level of a template DNA can be quantitatively determined accurately by monitoring the fluorescence intensity in real time, and therefore the method is effective for detecting *Mycobacterium tuberculosis*.

Example 4

Simultaneous diagnosis (discriminative diagnosis) between tuberculosis and non-tuberculosis Mycobacteriosis (NTM) involving *Mycobacterium tuberculosis* and *Mycobacterium avium* (*M. avium*), *Mycobacterium intracellulare* (*M. intracellulare*) or *Mycobacterium kansasii* (*M. kansasii*) was attempted by utilizing multiplex PCR, which was a method simultaneously amplifying multiple fragments in a single tube using plural pairs of the primer.

(1) Synthesis of Primer (i) Synthesis of PCR Primer for Detecting *Mycobacterium tuberculosis*

IS_F5 (SEQ ID NO: 1) and IS_R6 (SEQ ID NO:4) were prepared by the same method as in Example 1 (1), and used for the forward primer and the reverse primer.

(ii) Synthesis of PCR Primer for Detecting *M. avium*

MAV19K F1 (CGGCTGTTCGAGTGGCAACAAGTC shown as SEQ ID NO:15 in the present specification, hereinafter designates as "primer Fw for detecting *M. avium*") and MAV19K R1 (CCGTCGATGATGACCTTGGTCCC shown as SEQ ID NO:16, hereinafter designates as "primer Rv for detecting *M. avium*"), which were "the oligonucleotide primers specific to avium 19 kDa protein gene region" described in claim 5 of JP-A-11-69999, were prepared by the same method as in Example 1 (1), and used as the forward primer and the reverse primer.

(iii) Synthesis of PCR Primer for Detecting *M. intracellulare*

The sequence rps1 F 1 (CGGGACAAGGTCGCCAAGGTCAAGA shown as SEQ ID NO: 17 in the present specification, hereinafter designates as "primer Fw for detecting *M. intracellulare*") and the sequence rps1 R1 (GGGATG-TAGGCCGTCACCTCAAC shown as SEQ ID NO: 18, hereinafter designates as "primer Rv for detection of *M. intracellulare*"), which were "the oligonucleotide primers specific to intracellulare ribosome protein s1 gene region" described in claim 6 of JP-A-11-69999, were prepared by the same method as in Example 1 (1), and used as the forward primer and the reverse primer.

(iv) Synthesis of PCR Primer for Detecting *M. kansasii*

The sequence (GTCCCTGGCTGCTCTTGA shown as SEQ ID NO:19 of the present specification, hereinafter designates as "primer Fw for detecting *M. kansasii*"), which was the sequence in which one base was shifted to 5'-direction in Primer 15 which is designed from KATS2 sequence of *M. kansasii* described in FIG. 1 of JP-A-11-155589, and Primer E3 (GCTGGTGGAGATGGAGATGTT shown as SEQ ID NO:20 of the present specification, hereinafter designates as "primer Rv for detecting *M. kansasii*") were prepared by the same method as in Example 1 (1), and used as the forward primer and the reverse primer.

(2) Preparation of Samples

DNA samples of *Mycobacterium tuberculosis, M. avium, M. intracellulare* and *M. kansasii* obtained in Example 1 (2) were used.

(3) PCR

A solution containing 1 μM each of final concentration of the forward primer and the reverse primer synthesized hereinabove (1), 10 mM of Tris-HCl (pH 8.9), 1.5 mM of MgCl$_2$, 80 mM of KCl, 500 pg/mL of BSA, 0.1% of sodium cholate, 0.1% of Triton X-10, 0.2 mM each of dATP, dCTP, dGTP, dTTP and 40 units/mL of Taq polymerase (Nippon Gene Co. Ltd.) was prepared, and used as a reaction solution for RCR.

Samples for PCR (1) to (7) were prepared by adding 1 μL (0 to 1000 copies) each of the DNA sample to 20 μL of the reaction solution for PCR as shown in Table 1 below, and PCR was performed for each sample by using the same equipment used in Example 1 (3) under the same reaction conditions. In this connection, in Table 1, each of the terms, avium, intracellulare and kansasii indicates *M. avium, M. intracellulare* and *M. kansasii*, respectively. In the same way, x indicates without addition of DNA sample; ○ indicates with addition of DNA sample; and the number in parentheses below the mark ○ indicates concentration of added DNA sample (copy number).

In FIG. 5, the number in each lane shows the results obtained by using each 7 type of DNA sample (1) to (7) in Table 1 hereinabove.

Further, when DNA sample derived from *Mycobacterium tuberculosis* is present in the DNA sample, amplification product with 193 by is predicted to be obtained in PCR using IS_F5 primer and IS_R6 primer. When DNA sample derived from *M. avium* is present in the DNA sample, amplification product with 106 bp is predicted to be obtained in PCR using the primer Fw for detecting *M. avium* and the primer Rv for detecting *M. avium*. When DNA sample derived from *M. intracellulare* is present in the DNA sample, amplification product with 160 bp is predicted to be obtained in PCR using the primer Fw for detecting *M. intracellulare* and the primer Rv for detecting *M. intracellulare*. When DNA sample of *M. kansasii* is present in the DNA sample, amplification product with 235 by is predicted to be obtained in PCR using the primer Fw for detecting *M. kansasii* and the primer Rv for detecting *M. intracellulare. M. kansasii*. Therefore, in the side of the electrophoretic patterns in FIG. 5, an appearance order of each fraction of the amplification product is shown together with the direction of electrophoretic migration. Each of the terms, "*kansasii*", "TB", "intra" and "*avium*", indicates *M. kansasii, M. tuberculosis, M. intracellulare* and *M. avium*, respectively.

As is clear from FIG. 5, when PCR was performed at the same time by adding all DNA samples derived from *M. tuberculosis, M. avium, M. intracellulare* and *M. kansasii* in a single tube, all four fluorescent bands corresponding to the amplified products, which were predicted to be amplified when corresponding bacterial cells were present, were able to be confirmed (lanes (2) and (5)). Since the band of *Mycobacterium tuberculosis* was confirmed in the lane (5), it was found that even the concentration of DNA sample was ¹⁄₁₀₀ of the case of the lane (2), detection of *Mycobacterium tuberculosis* can be made with high sensitivity.

When PCR was performed using only the DNA sample derived from *Mycobacterium tuberculosis*, even when the primers for detecting *M. avium, M. intracellulare* and *M. kansasii* were present, only the fluorescent band corresponding to 193 bp which is a product of PCR reaction using IS_F5 and IS_R6 which are the primers for detecting *Mycobacterium tuberculosis* of the present invention (lane (3)).

Contrary to that, when PCR was performed by using samples without containing DNA sample derived from *Myco-*

TABLE 1

| | addition of DNA sample | | | | | | |
|---|---|---|---|---|---|---|---|
| DNA sample | (1) | (2) | (3) | (4) | (5) | (6) | (7) |
| kansasii | x | ○ (1000 copies) | x | ○ (1000 copies) | ○ (1000 copies) | x | ○ (1000 copies) |
| M. tuberculosis | x | ○ (1000 copies) | ○ (1000 copies) | x | ○ (10 copies) | x | ○ (1000 copies) |
| intracellulare | x | ○ (1000 copies) | x | ○ (1000 copies) | ○ (1000 copies) | x | ○ (1000 copies) |
| avium | x | ○ (1000 copies) | x | ○ (1000 copies) | ○ (1000 copies) | ○ (1000 copies) | x |

(4) Detection

Detection was performed by the same method as in Example 1 (4), that is, 1.5% agarose electrophoresis, ethidium bromide staining and detection of ultraviolet induced fluorescence.

(5) Results

Thus obtained results of the electrophoresis are shown in FIG. 5.

*bacterium tuberculosis* (lanes (4) and (6)), the fluorescent band corresponding to 106 bp derived from the PCR using primer Fw/Rv for detecting *M. avium*, the fluorescent band corresponding to 160 bp derived from PCR using primer Fw/Rv for detecting *M. intracellulare*, and the fluorescent band corresponding to 235 bp derived from PCR using primer Fw/Rv for detecting *M. kansasii* could be observed in the case when PCR using corresponding each DNA sample was performed, respectively, however, the fluorescent band corresponding to 193 bp, which was to be observed in case when *Mycobacterium tuberculosis* is present, could not be detected.

As is clear from hereinabove, it is understood that the specific detection of *Mycobacterium tuberculosis* is possible by using the primer of the present invention, even though DNA samples derived from plural kind of bacteria are present in a same single tube. Further, by performing the PCR with one tube reaction, genome DNA derived from each of four causative bacteria, i.e. *Mycobacterium tuberculosis*, MAC group (*M. avium* and *M. intracellulare*), which were causative bacteria of non-tuberculosis mycobacteriosis, and *M. kansasii*, could be detected simultaneously.

Example 5

Simultaneous diagnosis (discriminative diagnosis) between tuberculosis and non-tuberculosis mycobacteriosis (NTM) was attempted by performing multiplex PCR using the fluorescence labeled probe in the real time PCR amplification. The subject of the diagnosis are *Mycobacterium tuberculosis*, *Mycobacterium avium* (*M. avium*), *Mycobacterium intracellulare* (*M. intracellulare*) and *Mycobacterium kansasii* (*M. kansasii*)

(1) Primer for PCR
(i) PCR Primer for Detecting *Mycobacterium tuberculosis*

IS_F5 (SEQ ID NO: 1) and IS_R5 (SEQ ID NO:3) were prepared by the same method as in Example 1 (1), and used for the forward primer and the reverse primer.
(ii) PCR Primer for Detecting *M. avium*

The same primer as of Example 4 (1) (ii) was used.
(iii) PCR primer for detecting *M. intracellulare*

The same primer as of Example 4 (1) (iii) was used.
(iv) PCR primer for detecting *M. kansasii*

The same primer as of Example 4 (1) (iv) was used.
(2) Preparation of Probe
(i) Preparation of the Probe for Detecting *Mycobacterium tuberculosis*

The sequence "ACCGACGCCTACGCTCGCAG" for utilizing as the probe was designed from the oligonucleotide sequence of SEQ ID NO:6 which would be amplified by PCR using IS_F5 and IS_R5 as the primer, and the oligonucleotide having this sequence was synthesized (hereinafter designates as IS_F5R5FANTAM, SEQ ID NO: 11). A reporter dye FAM was linked to 5'-terminal of this oligonucleotide and the reporter quencher TAMRA was linked to 3'-terminal to obtain a labeled oligonucleotide probe (TaqMan™ fluorescent labeled probe, Applied Biosystems Japan Inc.).
(ii) Preparation of the Probe for Detecting *Mycobacterium avium*

The sequence "CAGCTCGAGCACCAGTGCGTCGG" for utilizing as the probe was designed from the oligonucleotide sequence which would be amplified by PCR using the primer Fw for detecting *M. avium* and the primer Rv for detecting *M. avium* as the primer, and the oligonucleotide having this sequence was synthesized (hereinafter designates as Mab_F1R1m2_Cy5BHQ, SEQ ID NO:21). The reporter dye Cy5 was linked to 5'-terminal of this oligonucleotide and the reporter quencher BHQ2 was linked to 3'-terminal to obtain a labeled oligonucleotide probe (dual terminal-labeled probe for real time PCR, SIGMA GENOSYSInc.).
(iii) Preparation of the Probe for Detecting *M. intracellulare*

The sequence "CTGGCTCGTCAGCTTCACGCG" for utilizing as the probe was designed from the oligonucleotide sequence which would be amplified by PCR using the primer Fw for detecting *M. intracellulare* and the primer Rv for detecting *M. intracellulare* as the primer, and the oligonucleotide having this sequence was synthesized (hereinafter designates as Int_F1R1m_VICMGB, SEQ ID NO:22). The reporter dye VIC was linked to 5'-terminal of this oligonucleotide and the reporter quencher MGB was linked to 3'-terminal to obtain a labeled oligonucleotide probe (TaqMan™ fluorescent labeled probe, Applied Biosystems Japan Inc.).
(iv) Preparation of Probe for Detecting *M. kansasii*

The sequence "ATCGTATCCACCATCCTCGA-CAGCGT" for utilizing as the probe was designed from the oligonucleotide sequence which would be amplified by PCR using the primer Fw for detecting *M. kansasii* and the primer Rv for detecting *M. kansasii* as the primer, and the oligonucleotide having this sequence was synthesized (hereinafter designates as KATS2_TAMBHQ2, SEQ ID NO:23). The reporter dye TAMRA was linked to 5'-terminal of this oligonucleotide and the reporter quencher BHQ2 was linked to 3'-terminal to obtain a labeled oligonucleotide probe (dual terminal-labeled probe for real time PCR, SIGMA GENOSYSInc.).
(3) Preparation of Sample With regard to the DNA samples obtained from *Mycobacterium tuberculosis*, *M avium*, *M. intracellulare* and *M. kansasii* prepared in Example 1 (2), an amount of DNA in each sample was measured by measuring absorbance. Amount of genome DNA (genome copy number) in the sample were determined by comparing the amount of DNA obtained with the known amount of genome DNA of *Mycobacterium tuberculosis*. Genome DNA having 108 copies/μL was obtained.

Subsequently, the DNA sample was diluted to give dilution series of $10^5$, $10^4$, $10^3$, $10^2$, 10, 5, and 2 copies/μL by using 10 mM of Tris-HCl buffer, pH 8.9 to prepare DNA sample for PCR.
(4) Detection by Real Time PCR A solution containing 1 μM each in final concentration of the forward primer and the reverse primer synthesized hereinabove (1), 195 nM each in final concentration of fluorescence labeled probe, 10 mM of Tris-HCl (pH 8.9), 1.5 mM of $MgCl_2$, 80 mM of KCl, 500 μg/mL of BSA, 0.1% of sodium cholate, 0.1% of Triton X-10 100, 0.2 mM each of dATP, dCTP, dGTP, dTTP and 40 units/mL of Taq polymerase (Nippon Gene Co. Ltd.) was prepared, and used as a reaction solution.

A solution prepared by adding 1 μL of DNA sample of each dilution series to 20 μL of the reaction solution was used as the sample for PCR. The sample for PCR was added to the well of 96 well reaction plate (MicroAmp Optical 96 well Reaction Plate, Applied Biosystems Japan, Inc.), and the real time PCR was performed by using the Thermal Cycler—Sequence detection System specified to TaqMan™ PCR (ABI7000, Applied Biosystems Japan, Inc.). PCR cycling conditions were 95° C. for 10 minutes for keeping warm, followed by 50 cycles of reaction at 95° C. for 15 seconds and at 60° C. for 1 minute, with measurement of fluorescence value generated from the reporter dye in each cycle.

The fluorescence value was measured on every one plate of the 96 well reaction plate for the measurement by using the function of Thermal Cycler for digitalizing the relative ratio of fluorescence intensity used in the measurement.
(5) Results and Analyses Since the reporter dyes of the primer for detecting each bacterial cell are different from each other, when fluorescence value from different four wavelengths derived from each reporter dye are monitored in every each cycle, amplification of DNA fragment targeted for genome sequence derived from *Mycobacterium tuberculosis* and amplification of genome DNA derived from four causative bacteria including non-tuberculosis mycobacteriosis, MAC group (*M. avium* and *M. intracellulare*) and *M. kansasii* can be confirmed.

Therefore, the fluorescence value generated from each reporter dye is measured. And then, an amplification curve indicating a relationship between the dilution series of genome DNA derived from each bacterium and the fluorescence value generated from each reporter dye was prepared by the same method as in Example 3 (5). Ct value (y-axis) versus the copy number of genome (x-axis, logarithmic expression) was plotted by the same method as in Example 3 (5) from the obtained amplification curve and the approximated curve obtained to each Ct value was used as the calibration curve. The results are shown in FIG. 6.

As is clear from the results (calibration curve) on DNA of *M. tuberculosis* in FIG. 6, it is understood that since the fluorescence from the reporter dye of the primer for detecting *Mycobacterium tuberculosis* could be detected, even though DNAs derived from plural kinds of bacterial cells other than *Mycobacterium tuberculosis* were present in a same single tube, *Mycobacterium tuberculosis* can be detected by using the oligonucleotide of the present invention as the primer, designing a labeled probe from the sequence to be the amplification region thereof, and performing the real time PCR.

In addition, since the calibration curve was able to be prepared, it is understood that *Mycobacterium tuberculosis* can be quantitatively determined by applying the real time PCR using the primer and the probe of the present invention. Further, it can be understood from FIG. 6 that *Mycobacterium tuberculosis* can be detected by the real time PCR using the primer and the probe of the present invention, even under the condition in which only two copies of genome DNA from *Mycobacterium tuberculosis* are present as the initial level (2 copies/reaction).

Further, when the real time PCR is utilized, since an initial level of template DNA can be quantitatively determined accurately by monitoring the fluorescence intensity in real time, therefore, the method is effective for detecting *Mycobacterium tuberculosis*.

Still further, even when genome DNAs derived from each of MAC group (*M. avium* and *M. intracellulare*) which are causative bacteria of non-tuberculosis mycobacteriosis, and *M. kansasii* are mixed each other (concurrent infection), linearity of each calibration curve is maintained without interfering each other's amplification reaction, and as a result, genome DNA derived from each of four causative bacteria can be monitored in the single tube reaction. detection sensitivity with 2 copies/reaction in this case can be presented in any bacterial species. Namely, it can be understood that detection of *Mycobacterium tuberculosis* and identification of non-tuberculous mycobacteria can be carried out simultaneously by performing real time PCR for a specimen in which plural numbers of bacterial cells are mixed each other,

INDUSTRIAL APPLICABILITY

According to the method for detecting *Mycobacterium tuberculosis* of the present invention, false positive on the diagnosis can be excluded, and as a result, detection of *Mycobacterium tuberculosis* with higher specificity and accuracy becomes possible, as compared with the conventional method of tubercular bacillus targeting IS6110.

Further, since the detection method of the present invention is specific to *Mycobacterium tuberculosis*, detection of *Mycobacterium tuberculosis* and simultaneous diagnosis (discriminative diagnosis) of non-tuberculous mycobacteria can be performed using one sample by conducting the detection of *Mycobacterium tuberculosis* using the primer and the probe of the present invention by the real time PCR.

What is claimed is:

1. An isolated or purified oligonucleotide consisting of a nucleic acid sequence selected from the nucleic acid sequence described in SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or the complementary sequence thereof, wherein the oligonucleotide has a property of hybridizing with the nucleic acid sequence of IS6110 gene in *Mycobacterium tuberculosis*.

2. A primer for detecting *Mycobacterium tuberculosis* comprising a nucleic acid sequence selected from the nucleic acid sequence described in SEQ ID NO:1, SEQ ID NO:2, SEQ ID NO:3, SEQ ID NO:4, or SEQ ID NO:5, or the complementary sequence thereof, wherein the primer has a property of hybridizing with the nucleic acid sequence of IS6110 gene in *Mycobacterium tuberculosis*.

3. The primer according to claim 2, wherein the primer is labeled with a labeling substance.

4. The primer according to claim 3, wherein the labeling substance is selected from a radioisotope, an enzyme, a fluorescent substance, a luminescent substance, and a biotin.

5. A probe for detecting *Mycobacterium tuberculosis* comprising a nucleic acid sequence selected from the nucleic acid sequence described in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:11, or the complementary sequence thereof, wherein the probe has a property of hybridizing with the nucleic acid sequence of IS6110 gene in *Mycobacterium tuberculosis*.

6. The probe according to claim 5, wherein the probe is labeled with a labeling substance.

7. The probe according to claim 6, wherein the labeling substance is selected from a radioisotope, an enzyme, a fluorescent substance, a luminescent substance, and a biotin.

8. The probe according to claim 6, wherein the probe is labeled with a reporter fluorescent dye and with a quencher dye.

9. A kit for detecting *Mycobacterium tuberculosis* comprising:
at least one of a primer pair or a probe;
wherein the primer pair comprises a first primer comprising a nucleic acid sequence selected from the nucleic acid sequence described in SEQ ID NO:1 or SEQ ID NO:2, or the complementary sequence thereof, and a second primer comprising a nucleic sequence selected from the nucleic acid sequence described in SEQ ID NO:3 or SEQ ID NO:4, or the complementary sequence thereof;
wherein the probe comprises a nucleic acid sequence selected from the nucleic acid sequence described in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:11, or the complementary sequence thereof; and
wherein the primer and the probe have a property of hybridizing with the nucleic acid sequence of IS6110 gene in *Mycobacterium tuberculosis*.

10. The kit according to claim 9, wherein the first or second primer is labeled with a labeling substance.

11. The kit according to claim 9, wherein the probe is labeled with a labeling substance.

12. The kit according to claim 9, comprising the primer pair and the probe, wherein the probe is labeled with a reporter fluorescent dye and with a quencher dye, and wherein the probe does not have the same nucleic acid sequence as the first and second primers.

13. The probe according to claim 8, wherein the 5'-terminal is labeled with a reporter fluorescent dye and the 3'-terminal is labeled with a quencher dye.

14. The oligonucleotide according to claim 1, wherein the oligonucleotide is obtained using a DNA synthesizer.

15. The primer according to claim 2, wherein the primer comprises an oligonucleotide portion consisting of the nucleic acid sequence described in SEQ ID NO:1, SEQ ID NO:2, SEQ ID NO:3, SEQ ID NO:4, or SEQ ID NO:5, or the complementary sequence thereof.

16. The primer according to claim 15, further comprising a labeling substance.

17. The probe according to claim 5, wherein the probe comprises an oligonucleotide portion consisting of the nucleic acid sequence described in SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:11, or the complementary sequence thereof.

18. The probe according to claim 17, further comprising a labeling substance.

19. The probe according to claim 18, wherein the probe is labeled with a labeling substance selected from a radioisotope, an enzyme, a fluorescent substance, a luminescent substance, and a biotin.

20. The probe according to claim 17, wherein the probe is labeled with a reporter fluorescent dye and with a quencher dye.

21. The probe according to claim 20, wherein the 5'-terminal is labeled with a reporter fluorescent dye and the 3'-terminal is labeled with a quencher dye.

22. The kit according to claim 12, wherein the primer pair comprises the first primer comprising an oligonucleotide portion consisting of the nucleic acid sequence described in SEQ ID NO:1 and the second primer comprising an oligonucleotide portion consisting of the nucleic sequence described in SEQ ID NO:3, and wherein the probe comprises an oligonucleotide portion consisting of the nucleic acid sequence described in SEQ ID NO:11.

* * * * *

SEQUENCE LISTING

<160> NUMBER OF SEQ ID NOS: 23

<210> SEQ ID NO 1
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 1
tgggtagcag acctcaccta t                                        21

<210> SEQ ID NO 2
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 2
acctcaccta tgtgtcgacc                                          20

<210> SEQ ID NO 3
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 3
cgagtacgct tcttgttgg                                        20

<210> SEQ ID NO 4
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 4
aacgtctttc aggtcgagta cg                                    22

<210> SEQ ID NO 5
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 5
tggcgttgag cgtagtagg                                        19

<210> SEQ ID NO 6
<211> LENGTH: 178
<212> TYPE: DNA
<213> ORGANISM: Artificial Sequence
<220> FEATURE:
<223> OTHER INFORMATION: oligonucleotide

<400> SEQUENCE: 6
tgggtagcag acctcaccta tgtgtcgacc tgggcagggt tcgcctacgt ggcctttgtc     60
accgacgcct acgctcgcag gatcctgggc tggcgggtcg cttccacgat ggccacctcc    120
atggtcctcg acgcgatcga gcaagccatc tggacccgcc aacaagaaag cgtactcg     178

<210> SEQ ID NO 7
<211> LENGTH: 182
<212> TYPE: DNA
<213> ORGANISM: Artificial Sequence
<220> FEATURE:
<223> OTHER INFORMATION: oligonucleotide

<400> SEQUENCE: 7
acctcaccta tgtgtcgacc tgggcagggt tcgcctacgt ggcctttgtc accgacgcct     60
acgctcgcag gatcctgggc tggcgggtcg cttccacgat ggccacctcc atggtcctcg    120
acgcgatcga gcaagccatc tggacccgcc aacaagaaag cgtactcgac ctgaaagacg    180
tt                                                                   182

<210> SEQ ID NO 8
<211> LENGTH: 324
<212> TYPE: DNA
<213> ORGANISM: Artificial Sequence
<220> FEATURE:
<223> OTHER INFORMATION: oligonucleotide

<400> SEQUENCE: 8
cgtactcgac ctgaaagacg ttatccacca tacggatagg ggatctcagt acacatcgat     60
ccggttcagc gagcggctcg ccgaggcagg catccaaccg tcggtcggag cggtcggaag    120
ctcctatgac aatgcactag ccgagacgat caacggccta tacaagaccg agctgatcaa    180
acccggcaag ccctggcggt ccatcgagga tgtcgagttg gccaccgcgc gctgggtcga    240
ctggttcaac catcgccgcc tctaccagta ctgcggcgac gtcccgccgg tcgaactcga    300

```
ggctgcctac tacgctcaac gcca                                          324

<210> SEQ ID NO 9
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 9
ttcggaccac cagcacctaa cc                                            22

<210> SEQ ID NO 10
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 10
ccttcttgtt ggcgggtcca g                                             21

<210> SEQ ID NO 11
<211> LENGTH: 20
<212> TYPE: DNA
<213> ORGANISM: Artificial Sequence
<220> FEATURE:
<223> OTHER INFORMATION: oligonucleotide probe

<400> SEQUENCE: 11
accgacgcct acgctcgcag                                               20

<210> SEQ ID NO 12
<211> LENGTH: 195
<212> TYPE: DNA
<213> ORGANISM: Mycobacterium tuberculosis

<400> SEQUENCE: 12
cggaccacca gcacctaacc ggctgtgggt agcagacctc acctatgtgt cgacctgggc   60
agggttcgcc tacgtggcct tgtcaccga cgcctacgct cgcaggatcc tgggctggcg   120
ggtcgcttcc acgatggcca cctccatggt cctcgacgcg atcgagcaag ccatctggac   180
ccgccaacaa gaagg                                                    195

<210> SEQ ID NO 13
<211> LENGTH: 195
<212> TYPE: DNA
<213> ORGANISM: Mycobacterium triviale

<400> SEQUENCE: 13
cggaccacca gcacctaacc gcttgtgggt ggccgacttc acgtatgtgt ccacatggtc   60
gggctggtgc tacaccgcgt tcgtcatcga cgcctacgcc cgccgcatcc tgggctggtc   120
ggtggcgacc accatgacca gccaactggt cgtcgacgcc gtcgaccagg cgatctggac   180
ccgccaacaa gaagg                                                    195

<210> SEQ ID NO 14
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 14
```
ttgcagaaag tccagctcat gc                                              22

<210> SEQ ID NO 15
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 15
cggctgttcg agtggcaaca agtc                                            24

<210> SEQ ID NO 16
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 16
ccgtcgatga tgaccttggt ccc                                             23

<210> SEQ ID NO 17
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 17
cgggacaagg tcgccaaggt caaga                                           25

<210> SEQ ID NO 18
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 18
gggatgtagg ccgtcacctc aac                                             23

<210> SEQ ID NO 19
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 19
gtccctggct gctcttga                                                   18

<210> SEQ ID NO 20
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 20
gctggtggag atggagatgt t                                               21

<210> SEQ ID NO 21
<211> LENGTH: 23
<212> TYPE: DNA
<213> ORGANISM: Artificial Sequence

```
<220> FEATURE:
<223> OTHER INFORMATION: oligonucleotide probe

<400> SEQUENCE: 21
cagctcgagc accagtgcgt cgg                                        23

<210> SEQ ID NO 22
<211> LENGTH: 21
<212> TYPE: DNA
<213> ORGANISM: Artificial Sequence
<220> FEATURE:
<223> OTHER INFORMATION: oligonucleotide probe

<400> SEQUENCE: 22
ctggctcgtc agcttcacgc g                                          21

<210> SEQ ID NO 23
<211> LENGTH: 26
<212> TYPE: DNA
<213> ORGANISM: Artificial Sequence
<220> FEATURE:
<223> OTHER INFORMATION: oligonucleotide probe

<400> SEQUENCE: 23
atcgtatcca ccatcctcga cagcgt                                     26
```